United States Patent [19]

Dalla-Favera et al.

[11] Patent Number: 5,888,820
[45] Date of Patent: Mar. 30, 1999

[54] RETROVIRAL VECTOR CAPABLE OF TRANSDUCING THE ALDEHYDE DEHYDROGENASE-1 GENE AND USES OF SAID VECTOR

[75] Inventors: Riccardo Dalla-Favera, New York, N.Y.; Alessandro Massimo Gianni, Milan, Italy

[73] Assignee: The Trustees of Columbia University in the City of New York, New York, N.Y.

[21] Appl. No.: 347,326

[22] PCT Filed: Apr. 1, 1994

[86] PCT No.: PCT/US94/03624

§ 371 Date: Dec. 1, 1994

§ 102(e) Date: Dec. 1, 1994

[87] PCT Pub. No.: WO94/23015

PCT Pub. Date: Oct. 13, 1994

Related U.S. Application Data

[63] Continuation-in-part of Ser. No. 41,722, Apr. 1, 1993, abandoned.

[51] Int. Cl.$^6$ ............................. C12N 15/00; C12N 15/63
[52] U.S. Cl. .................... 435/456; 435/172.3; 435/320.1
[58] Field of Search ............................... 435/320.1, 172.3

[56] References Cited

PUBLICATIONS

Narahanan et al. Deveopment of an amphotropic, high–titer retrovirus vector expressing the dihydrofolate reductase gene and conferring methotrexate resistance, Gene 48:71–80, 1986.

Russo et al. Characterization of cytosolic aldehyde dehydrogenase from cyclophosphamide resistant L1210 cells, Cancer Research 48:2963–2968, 1988.

Bregni, M., et al. (1992) "Human Peripheral Blood Hematopoietic Progenitors Are Optimal Targets Of Retroviral–Mediated Gene Transfer." *Blood* 80: 1418–1422.

Canellos, G.P., et al. (1970) "Combination Chemotherapy For Metastatic Breast Carcinoma." *Cancer* 38: 1882–1886 (Exhibit B).

Correll, P.H., et al. (1989) "Production of Human Glucocerebrosidase In Mice After Retroviral Gene Transfer Into Multipotential Hematopoietic Progenitor Cells." *Proc. Natl. Acad. Sci. U.S.A.* 86: 8912–8916 (Exhibit C).

Gianni, A.M., et al. (1989) "Granulocyte–Macrophage Colony–Stimulating Factor Two Harvest Circulating Haemopoietic Stem Cells For Autotransplantation." *The Lancet* 2: 580–585.

Hempel, J., et al., (1984) "Aldehyde Dehydrogenase From Human Liver." *Eur. J. BioChem.* 141: 21–35.

Hsu, L.C., et al. (1989) "Genomic Structure Of The Human Cytosolic Aldehyde Dehydrogenase Gene." *Genomics* 5: 857–865.

Hsu, L.C., et al. (1985) "Cloning of cDNAs For Human Alhehyde Dehydrogenases 1 And 2." *Proc. Natl. Acad. Sci. U.S.A.* 82: 3771–3775.

Mann, R., et al. (1983) "Construction Of A Retrovirus Packaging Mutant And Its Use To Produce Helper–Free Defective Retrovirus." *Cell* 33: 153–159.

Miller, A.D. and C. Buttmore (1986) "Redesign Of Retrovirus Packaging Cell Lines To Avoid Recombination Leading To Helper Virus Production." *Molecular and Cellular Biology* 6: 2895–2902.

Miller, A.D. and G.J. Rosman (1989) "Improved Retroviral Vectors For Gene Transfer And Expression." *BioTechniques* 7: 980–990.

Siena, S., et al. (1989) "Circulation of CD34 Hematopoietic Stem Cells In The Peripheral Blood of High–Dose Cyclophosphamide–Treated Patients: Enhancement By Intravenous Recombinant Human Granulocyte–Macrophage Colony–Stimulating Factor." *Blood* 74: 1905–1914.

*Primary Examiner*—Douglas W. Robinson
*Assistant Examiner*—Thanda Wai
*Attorney, Agent, or Firm*—John P. White; Cooper & Dunham LLP

[57] ABSTRACT

This invention provides viral and retroviral vectors which comprises a nucleic acid molecule encoding a human cytosolic aldehyde dehydrogenase or a glutamylcysteine synthetase or combinations thereof. Further, this invention provides an isolated mammalian nucleic acid molecule encoding a cytosolic aldehyde dehydrogenase and glutamylecysteine synthetase. In addition, this invention provides a method for reducing the toxic effects of a cyclophosphamide in a subject which comprises replacing the subject's hematopoietic cells with hematopoietic cells having the retroviral vector. Further, this invention provides a method for introducing a selectable marker into a mammalian cell which comprises transfecting the cell with a nucleic acid molecule encoding human cytosolic aldehyde dehydrogenase or glutamylcysteine synthetase. Lastly, this invention provides a method for selecting mammalian cells expressing protein of interest which comprises: a) introducing into the cells a nucleic acid molecule comprising a nucleic acid molecule encoding the protein of interest and the nucleic acid molecule encoding human cytosolic aldehyde dehydrogenase: b) culturing the resulting transfected cells; and c) selecting cells which express human cytosolic aldehyde dehdrogenase.

17 Claims, 31 Drawing Sheets

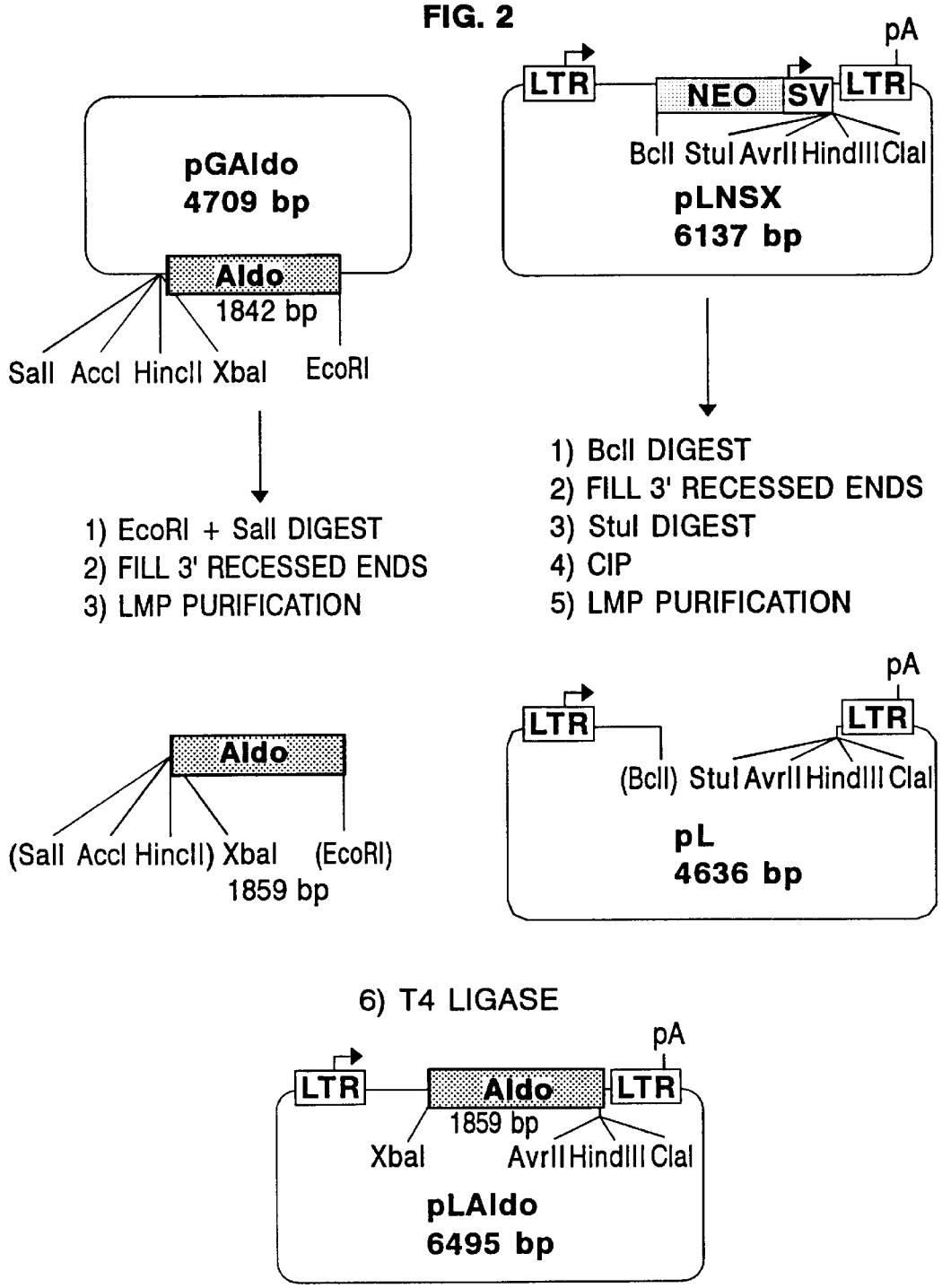

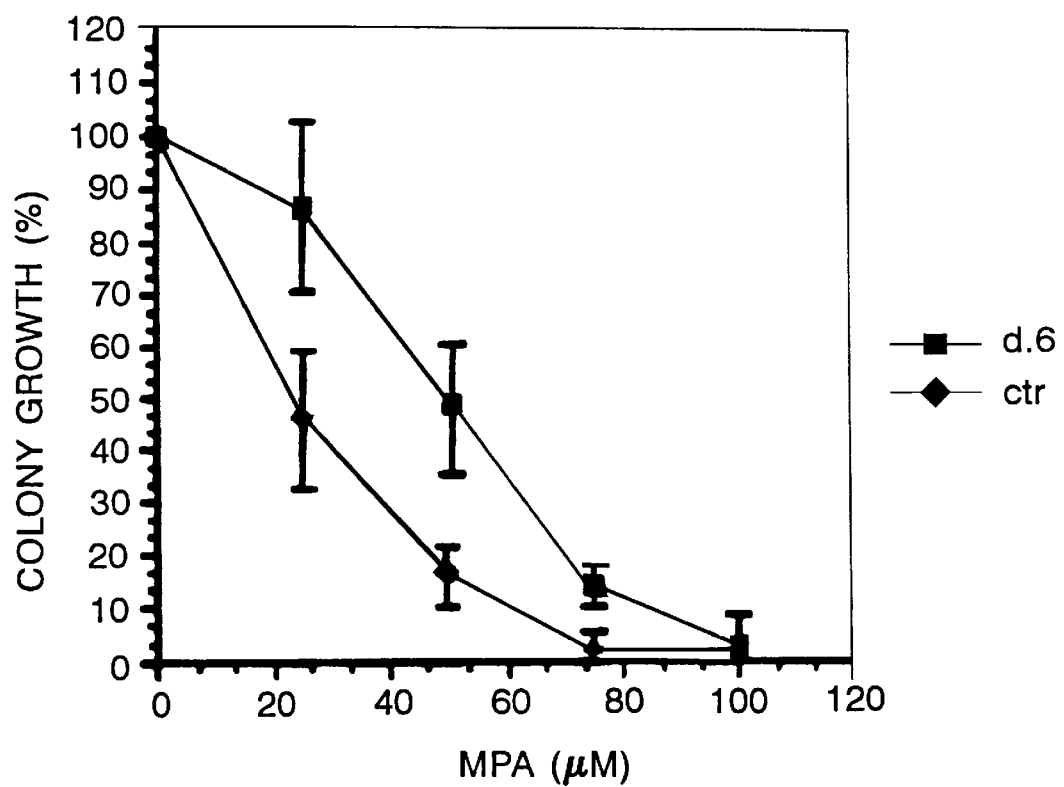

FIG. 4A

SEQ. ID. NO. 1

```
C TAG AAC CAA ATT GCT GAG CCA GTC ACC TGT GTT CCA GGA GCC GAA                      46
  Asn Gln Ile Ala Glu Pro Val Thr Cys Val Pro Gly Ala Glu
  1               5                  10                 15

TCA GAA ATG TCA TCC TCA GGC ACG CCA GAC TTA CCT GTC CTA CTC ACC                    94
Ser Glu Met Ser Ser Ser Gly Thr Pro Asp Leu Pro Val Leu Leu Thr
                20                  25                  30

GAT TTG AAG ATT CAA TAT ACT AAG ATC TTC ATA AAC AAT GAA TGG CAT                   142
Asp Leu Lys Ile Gln Tyr Thr Lys Ile Phe Ile Asn Asn Glu Trp His
            35                  40                  45

GAT TCA GTG AGT GGC AAG AAA TTT CCT GTC TTT AAT CCT GCA ACT GAG                   190
Asp Ser Val Ser Gly Lys Lys Phe Pro Val Phe Asn Pro Ala Thr Glu
        50                  55                  60

GAG CTC TGC CAG GTA GAA GGA GAT AAG GAG GAT GTT GAC AAG                           238
Glu Leu Cys Gln Val Glu Gly Asp Lys Glu Asp Val Asp Lys
    65                  70                  75
```

FIG. 4B

```
GCA GTG AAG GCC GCA AGA CAG GCT TTT CAG ATT GGA TCT CCG TGG CGT    286
Ala Val Lys Ala Ala Arg Gln Ala Phe Gln Ile Gly Ser Pro Trp Arg
 80                  85                  90                  95

ACT ATG GAT GCT TCC GAG AGG GGG CGA CTA TTA TAC AAG TTG GCT GAT    334
Thr Met Asp Ala Ser Glu Arg Gly Arg Leu Leu Tyr Lys Leu Ala Asp
                100                 105                 110

TTA ATC GAA AGA GAT CGT CTG CTG GCG ACA ATG GAG TCA ATG GAG TCA    382
Leu Ile Glu Arg Asp Arg Leu Leu Ala Thr Met Glu Ser Met Glu Ser
                115                 120                 125

ATG AAT GGT GGA AAA CTC TAT TCC AAT GCA TAT CTG AAT GAT TTA GCA    430
Met Asn Gly Gly Lys Leu Tyr Ser Asn Ala Tyr Leu Asn Asp Leu Ala
            130                 135                 140

GGC TGC ATC AAA ACA TTG CGC TAC TGT GCA GGT TGG GCT GAC AAG ATC    478
Gly Cys Ile Lys Thr Leu Arg Tyr Cys Ala Gly Trp Ala Asp Lys Ile
            145                 150                 155
```

FIG. 4C

| | | | | | | | | | | | | | | | |
|---|---|---|---|---|---|---|---|---|---|---|---|---|---|---|---|
| CAG | GGC | CAG | GGC | CGT | ACA | ATA | CCA | ATT | GAT | GGA | AAT | TTT | ACA | TAT | 526 |
| Gln | Gly | Gln | Gly | Arg | Thr | Ile | Pro | Ile | Asp | Gly | Asn | Phe | Thr | Tyr | |
| 160 | | | | | 165 | | | | 170 | | | | | 175 | |
| ACA | AGA | CAT | GAA | CCT | ATT | GGG | GTA | TGT | GGC | CAA | ATC | ATT | CCT | TGG | AAT | 574 |
| Thr | Arg | His | Glu | Pro | Ile | Gly | Val | Cys | Gly | Gln | Ile | Ile | Pro | Trp | Asn | |
| | | | | 180 | | | | | 185 | | | | | 190 | | |
| TTC | CCG | TTG | GTT | ATG | CTC | ATT | TGG | AAG | ATA | GGG | CCT | GCA | CTG | AGC | TGT | 622 |
| Phe | Pro | Leu | Val | Met | Leu | Ile | Trp | Lys | Ile | Gly | Pro | Ala | Leu | Ser | Cys | |
| | | 195 | | | | | 200 | | | | | 205 | | | | |
| GGA | AAC | ACA | GTG | GTC | AAA | CCA | GCA | GAG | CAA | ACT | CCT | CTC | ACT | GCT | 670 |
| Gly | Asn | Thr | Val | Val | Lys | Pro | Ala | Glu | Gln | Thr | Pro | Leu | Thr | Ala | |
| | 210 | | | | 215 | | | | 220 | | | | | | |
| CTC | CAC | GTG | GCA | TCT | TTA | ATA | AAA | GAG | GCA | GGG | TTT | CCT | GGA | GTA | 718 |
| Leu | His | Val | Ala | Ser | Leu | Ile | Lys | Glu | Ala | Gly | Phe | Pro | Gly | Val | |
| 225 | | | | | 230 | | | | | 235 | | | | | |
| GTG | AAT | ATT | GTT | CCT | GGT | TAT | GGG | CCT | ACA | GCA | GGG | GCA | GCC | ATT | TCT | 766 |

FIG. 4D

```
Val Asn Ile Val Pro Gly Tyr Gly Pro Thr Ala Gly Ala Ala Ile Ser
240                 245                 250                 255

TCT CAC ATG GAT ATA GAC AAA GTA GCC TTC ACA GGA TCA ACA GAG GTT     814
Ser His Met Asp Ile Asp Lys Val Ala Phe Thr Gly Ser Thr Glu Val
                    260                 265                 270

GGC AAG TTG ATC AAA GAA GCT GCC GGG AAA AGC AAT CTG AAG AGG GTG     862
Gly Lys Leu Ile Lys Glu Ala Ala Gly Lys Ser Asn Leu Lys Arg Val
                275                 280                 285

ACC CTG GAG CTT GGA GGA AAG AGC CCT TGC ATT GTG TTA GCT GAT GCC     910
Thr Leu Glu Leu Gly Gly Lys Ser Pro Cys Ile Val Leu Ala Asp Ala
                    290                 295                 300

GAC TTG GAC AAT GCT GTT GAA TTT GCA CAC CAT GGG GTA TTC TAC CAC     958
Asp Leu Asp Asn Ala Val Glu Phe Ala His His Gly Val Phe Tyr His
                305                 310                 315

CAG GGC CAG TGT TGT ATA GCC GCA TCC AGG ATT TTT GTG GAA GAA TCA    1006
Gln Gly Gln Cys Cys Ile Ala Ala Ser Arg Ile Phe Val Glu Glu Ser
320                 325                 330                 335
```

FIG. 4E

ATT TAT GAT GAG TTT GTT CGA AGG AGT GTT GAG CGG GCT AAG AAG TAT    1054
Ile Tyr Asp Glu Phe Val Arg Arg Ser Val Glu Arg Ala Lys Lys Tyr
                340                 345                 350

ATC CTT GGA AAT CCT CTG ACC CCA GGA GTC ACT CAA GGC CCT CAG ATT    1102
Ile Leu Gly Asn Pro Leu Thr Pro Gly Val Thr Gln Gly Pro Gln Ile
            355                 360                 365

GAC AAG GAA CAA TAT GAT AAA ATA CTT GAC CTC ATT GAG AGT GGG AAG    1150
Asp Lys Glu Gln Tyr Asp Lys Ile Leu Asp Leu Ile Glu Ser Gly Lys
        370                 375                 380

AAA GAA GGG GCC AAA CTG GAA TGT GGA GGC CCG TGG GGG AAT AAA        1198
Lys Glu Gly Ala Lys Leu Glu Cys Gly Gly Pro Trp Gly Asn Lys
    385                 390                 395

GGC TAC TTT GTC CAG CCC ACA GTG TTC TCT AAT GTT ACA GAT GAG ATG    1246
Gly Tyr Phe Val Gln Pro Thr Val Phe Ser Asn Val Thr Asp Glu Met
400                 405                 410                 415

FIG. 4F

```
CGC ATT GCC AAA GAG GAG ATT TTT GGA CCA GTG CAG CAA ATC ATG AAG    1294
Arg Ile Ala Lys Glu Glu Ile Phe Gly Pro Val Gln Gln Ile Met Lys
        420                 425                 430

TTT AAA TCT TTA GAT GAC GTG ATC AAA AGA GCA AAC AAT ACT TTC TAT    1342
Phe Lys Ser Leu Asp Asp Val Ile Lys Arg Ala Asn Asn Thr Phe Tyr
        435                 440                 445

GGC TTA TCA GCA GGA GTG TTT ACC AAA GAC ATT GAT AAA GCC ATA ACA    1390
Gly Leu Ser Ala Gly Val Phe Thr Lys Asp Ile Asp Lys Ala Ile Thr
        450                 455                 460

ATC TCT TCT GCT CTG CAG GCA GGA ACA GTG TGG GTG AAT TGC TAT GGC    1438
Ile Ser Ser Ala Leu Gln Ala Gly Thr Val Trp Val Asn Cys Tyr Gly
        465                 470                 475

GTA GTA AGT GCC CAG TGC CCC TTT GGT GGA TTC AAG ATG TCT GGA AAT    1486
Val Val Ser Ala Gln Cys Pro Phe Gly Gly Phe Lys Met Ser Gly Asn
        480                 485                 490                 495

GGA AGA GAA CTG GGA GAG TAC GGT TTC CAT GAA TAT ACA GAG GTC AAA    1534
Gly Arg Glu Leu Gly Glu Tyr Gly Phe His Glu Tyr Thr Glu Val Lys
```

FIG. 4G

```
Gly Arg Glu Leu Gly Gly Glu Tyr Gly Phe His Glu Tyr Thr Glu Val Lys
            500                     505                     510
ACA GTC ACA GTG AAA ATC TCT CAG AAG AAC TCA T AAAGAAAATA                      1578
Thr Val Thr Val Lys Ile Ser Gln Lys Asn Ser
            515                     520

CAAGAGTGGA GAGAAGCTCT TCAATAGCTA AGCATCTCCT TACAGTCACT AATATAGTAG            1638
ATTTTAAAGA CAAAATTTTT CTTTTCTTGA TTTTTTTTAA ACATAAGCTA AATCATATTA            1698
GTATTAATAC TACCCATAGA AAACTTGACA TGTAGCTTCT TCTGAAAGAA TTATTTGCCT            1758
TCTGAAATGT GACCCCCAAG TCCTATCCTA AATAAAAAAA GACAAATTCG GATGTATGAT            1818
CTCTCTAGCT TTGTCATAGT TATG                                                   1842
```

FIG. 5A

SEQ. ID. NO. 2

```
  1  Asn Gln Ile Ala Glu Pro Val Thr Cys Val Pro Gly Ala Glu Ser
                     5                  10                  15
     Glu Met Ser Ser Ser Gly Thr Pro Asp Leu Pro Val Leu Leu Thr Asp
                     20                  25                  30
     Leu Lys Ile Gln Tyr Thr Lys Ile Phe Ile Asn Asn Glu Trp His Asp
                     35                  40                  45
     Ser Val Ser Gly Lys Lys Phe Pro Val Phe Asn Pro Ala Thr Glu Glu
                     50                  55                  60
     Glu Leu Cys Gln Val Glu Gly Asp Lys Glu Asp Val Asp Lys Ala
                     65                  70                  75                  80
     Val Lys Ala Ala Arg Gln Ala Phe Gln Ile Gly Ser Pro Trp Arg Thr
                     85                  90                  95
```

FIG. 5B

Met Asp Ala Ser Glu Arg Gly Arg Leu Leu Tyr Lys Leu Ala Asp Leu
              100                 105                 110

Ile Glu Arg Asp Arg Leu Leu Ala Thr Met Glu Ser Met Glu Ser Met
              115                 120                 125

Asn Gly Gly Lys Leu Tyr Ser Asn Ala Tyr Leu Asn Asp Leu Ala Gly
              130                 135                 140

Cys Ile Lys Thr Leu Arg Tyr Cys Ala Gly Trp Ala Asp Lys Ile Gln
              145                 150                 155                 160

Gly Gln Gly Arg Thr Ile Pro Ile Asp Gly Asn Phe Phe Thr Tyr Thr
              165                 170                 175

Arg His Glu Pro Ile Gly Val Cys Gly Gln Ile Ile Pro Trp Asn Phe
              180                 185                 190

FIG. 5C

Pro Leu Val Met Leu Ile Trp Lys Ile Gly Pro Ala Leu Ser Cys Gly
195 200 205

Asn Thr Val Val Val Lys Pro Ala Glu Gln Thr Pro Leu Thr Ala Leu
210 215 220

His Val Ala Ser Leu Ile Lys Glu Ala Gly Phe Pro Pro Gly Val Val
225 230 235 240

Asn Ile Val Pro Gly Tyr Gly Pro Thr Ala Gly Ala Ala Ile Ser Ser
245 250 255

His Met Asp Ile Asp Lys Val Ala Phe Thr Gly Ser Thr Glu Val Gly
260 265 270

Lys Leu Ile Lys Glu Ala Ala Gly Lys Ser Asn Leu Lys Arg Val Thr
275 280 285

Leu Glu Leu Gly Gly Lys Ser Pro Cys Ile Val Leu Ala Asp Ala Asp
290 295 300

FIG. 5D

Leu Asp Asn Ala Val Glu Phe Ala His His Gly Val Phe Tyr His Gln
305                 310                 315                 320

Gly Gln Cys Cys Ile Ala Ala Ser Arg Ile Phe Val Glu Glu Ser Ile
            325                 330                 335

Tyr Asp Glu Phe Val Arg Arg Ser Val Glu Arg Ala Lys Lys Tyr Ile
        340                 345                 350

Leu Gly Asn Pro Leu Thr Pro Gly Val Thr Gln Gly Pro Gln Ile Asp
                355                 360                 365

Lys Glu Gln Tyr Asp Lys Ile Leu Asp Leu Ile Glu Ser Gly Lys Lys
370                 375                 380

Glu Gly Ala Lys Leu Glu Cys Gly Gly Gly Pro Trp Gly Asn Lys Gly
385                 390                 395                 400

Tyr Phe Val Gln Pro Thr Val Phe Ser Asn Val Thr Asp Glu Met Arg
        405                 410                 415

FIG. 5E

```
Ile Ala Lys Glu Glu Ile Phe Gly Pro Val Gln Gln Ile Met Lys Phe
            420                 425                 430
Lys Ser Leu Asp Asp Val Ile Lys Arg Ala Asn Asn Thr Phe Tyr Gly
            435                 440                 445
Leu Ser Ala Gly Val Phe Thr Lys Asp Ile Asp Lys Ala Ile Thr Ile
            450                 455                 460
Ser Ser Ala Leu Gln Ala Gly Thr Val Trp Val Asn Cys Tyr Gly Val
            465                 470                 475             480
Val Ser Ala Gln Cys Pro Phe Gly Gly Phe Lys Met Ser Gly Asn Gly
            485                 490                 495
Arg Glu Leu Gly Glu Tyr Gly Phe His Glu Tyr Thr Glu Val Lys Thr
            500                 505                 510
Val Thr Val Lys Ile Ser Gln Lys Asn Ser
            515                 520
```

FIG. 6A

SEQ. ID. NO.3

```
GAATTCCGGG CGGGAGCCGC CGCGGCAGCG CGGCCCGTGGG GTCCGCCGCC GCCGCATCGG    60
AGCGGGAGGA GGAGCAGCGG GGAGGGCGAG GCCGCCGGGC CCGCCCGGGC CGAGAGCCGT   120
CTCGGTCTTC TGCCTTCGCC TCCGCGCGGT GCGTCGGACC CAGGGTCTGT CACCTGGGCG   180
CCAGGGCCCG CCGCCGGGGA GCCGGAGCGG GCAGGACCCT CCCTCCGCCG ACTGCGGCCC   240
GAGAGCGCCC CCGCGGGGTG GAGCGGCAGC CGCCTTCTGC GGGCGGGCTGA GTGTCCGTCT   300
CGCGCCCGGA GCGGGCGACC GCCGTCAGCC CGGAGGAGGA GGAGGAGGAG GAGGGGGCGT   360
```

```
CC ATG GGG CTG CTG TCC CAG GGC TCG CCG CTG AGC TGG GAG GAA ACC    407
   Met Gly Leu Leu Ser Gln Gly Ser Pro Leu Ser Trp Glu Glu Thr
   1               5                   10                  15

AAG CGC CAT GCC GAC CAC GTG CGG CGG CAC GGG ATC CTC CAG TTC CTG    455
Lys Arg His Ala Asp His Val Arg Arg His Gly Ile Leu Gln Phe Leu
             20                  25                  30
```

FIG. 6B

```
CAC ATC TAC CAC GCC GTC AAG GAC CGG CAC AAG GAC GTT CTC AAG TGG       503
His Ile Tyr His Ala Val Lys Asp Arg His Lys Asp Val Leu Lys Trp
             35                  40                  45

GGC GAT GAG GTG GAA TAC ATG TTG GTA TCT TTT GAT CAT GAA AAT AAA       551
Gly Asp Glu Val Glu Tyr Met Leu Val Ser Phe Asp His Glu Asn Lys
         50                  55                  60

AAA GTC CGG TTG GTC CTG TCT GGG GAG AAA GTT CTT GAA ACT CTG CAA       599
Lys Val Arg Leu Val Leu Ser Gly Glu Lys Val Leu Glu Thr Leu Gln
     65                  70                  75

GAG AAG GGG GAA AGG ACA AAC CCA AAC CAT CCT ACC CTT TGG AGA CCA       647
Glu Lys Gly Glu Arg Thr Asn Pro Asn His Pro Thr Leu Trp Arg Pro
 80                  85                  90                  95

GAG TAT GGG AGT TAC ATG ATT GAA GGG ACA CCA GGA CAG CCC TAC GGA       695
Glu Tyr Gly Ser Tyr Met Ile Glu Gly Thr Pro Gly Gln Pro Tyr Gly
                100                 105                 110

GGA ACA ATG TCC GAG TTC AAT ACA GTT GAG GCC AAC ATG CGA AAA CGC       743
Gly Thr Met Ser Glu Phe Asn Thr Val Glu Ala Asn Met Arg Lys Arg
```

FIG. 6C

```
Gly Thr Met Ser Glu Phe Asn Thr Val Glu Ala Asn Met Arg Lys Arg
            115                 120                 125

CGG AAG GAG GCT ACT TCT ATA TTA GAA GAA AAT CAG GCT CTT TGC ACA       791
Arg Lys Glu Ala Thr Ser Ile Leu Glu Glu Asn Gln Ala Leu Cys Thr
        130                 135                 140

ATA ACT TCA TTT CCC AGA TTA GGC TGT CCT GGG TTC ACA CTG CCC GAG       839
Ile Thr Ser Phe Pro Arg Leu Gly Cys Pro Gly Phe Thr Leu Pro Glu
    145                 150                 155

GTC AAA CCC AAC CCA GTG GAA GGA GCT TCC AAG TCC CTC TTT TTT           887
Val Lys Pro Asn Pro Val Glu Gly Gly Ala Ser Lys Ser Leu Phe Phe
160                 165                 170                 175

CCA GAT GAA GCA ATA ATA AAC AAG CAC CCT CGC TTC AGT ACC TTA ACA AGA   935
Pro Asp Glu Ala Ile Ile Asn Lys His Pro Arg Phe Ser Thr Leu Thr Arg
        180                 185                 190

AAT ATC CGA CAT AGG AGA GGA GAA AAG GTT GTC ATC AAT CTA CCA ATA       983
Asn Ile Arg His Arg Arg Gly Glu Lys Val Val Ile Asn Leu Pro Ile
    195                 200                 205
```

FIG. 6D

```
TTT AAG GAC AAG AAT ACA CCA TCT CCA TTT ATA GAA ACA TTT ACT GAG    1031
Phe Lys Asp Lys Asn Thr Pro Ser Pro Phe Ile Glu Thr Phe Thr Glu
            210                 215                 220

GAT GAA GCT TCA AGG GCT GAA GCT TCT AAG CCG GAT CAT ATT TAC ATG GAT    1079
Asp Asp Glu Ala Ser Arg Ala Ser Lys Pro Asp His Ile Tyr Met Asp
        225                 230                 235

GCC ATG GGA TTT GGA ATG GGC AAT TGC TGT CTC CAG GTG ACA TTC CAA    1127
Ala Met Gly Phe Gly Met Gly Asn Cys Cys Leu Gln Val Thr Phe Gln
240                 245                 250                 255

GCC TGC AGT ATA TCT GAG GCC AGA TAC CTT TAT GAT CAG TTG GCT ACT    1175
Ala Cys Ser Ile Ser Glu Ala Arg Tyr Leu Tyr Asp Gln Leu Ala Thr
            260                 265                 270

ATC TGT CCA ATT GTT ATG GCT TTG AGT GCT GCA TCT CCC TTT TAC CGA    1223
Ile Cys Pro Ile Val Met Ala Leu Ser Ala Ala Ser Pro Phe Tyr Arg
        275                 280                 285
```

FIG. 6E

```
GGC TAT GTG TCA GAC ATT GAT TGT CGC TGG GGA GTG ATT TCT GCA TCT    1271
Gly Tyr Val Ser Asp Ile Asp Cys Arg Trp Gly Val Ile Ser Ala Ser
        290                 295                 300

GTA GAT GAT AGA ACT CGG GAG CGA GGA CTG GAG CCA TTG AAG AAC        1319
Val Asp Asp Arg Thr Arg Glu Arg Gly Leu Glu Pro Leu Lys Asn
    305                 310                 315

AAT AAC TAT AGG ATC AGT AAA TCC CGA TAT GAC TCA ATA GAC AGC TAT    1367
Asn Asn Tyr Arg Ile Ser Lys Ser Arg Tyr Asp Ser Ile Asp Ser Tyr
        320                 325                 330                 335

TTA TCT AAG TGT GGT GAG ATC AAA TAT AAT GAC ATC GAC TTG ACG ATA GAT 1415
Leu Ser Lys Cys Gly Glu Ile Lys Tyr Asn Asp Ile Asp Leu Thr Ile Asp
        340                 345                 350

AAA GAG ATC TAC GAA CAG CTG TTG CAG GAA GGC ATT GAT CAT CTC CTG    1463
Lys Glu Ile Tyr Glu Gln Leu Leu Gln Glu Gly Ile Asp His Leu Leu
        355                 360                 365

GCC CAG CAT GTT GCT CAT CTC TTT ATT AGA GAC CCA CTG ACA CTG TTT    1511
```

FIG. 6F

```
Ala Gln His Val Ala His Leu Phe Ile Arg Asp Pro Leu Thr Leu Phe
        370                 375                 380

GAA GAG AAA ATA CAC CTG GAT GAT GCT AAT GAG TCT GAC CAT TTT GAG    1559
Glu Glu Lys Ile His Leu Asp Asp Ala Asn Glu Ser Asp His Phe Glu
        385                 390                 395

AAT ATT CAG TCC ACA AAT TGG CAG ACA ATG AGA TTT AAG CCC CCT CCT    1607
Asn Ile Gln Ser Thr Asn Trp Gln Thr Met Arg Phe Lys Pro Pro Pro
400                 405                 410                 415

CCA AAC TCA GAC ATT GGA TGG AGA GTA GAA TTT CGA CCC ATG GAG GTG    1655
Pro Asn Ser Asp Ile Gly Trp Arg Val Glu Phe Arg Pro Met Glu Val
        420                 425                 430

CAA TTA ACA GAC TTT GAG AAC TCT GCC TAT GTG GTG TTT GTG GTA CTG    1703
Gln Leu Thr Asp Phe Glu Asn Ser Ala Tyr Val Val Phe Val Val Leu
        435                 440                 445

CTC ACC AGA GTG ATC CTT TCC TAC AAA TTG GAT TTT CTC ATT CCA CTG    1751
Leu Thr Arg Val Ile Leu Ser Tyr Lys Leu Asp Phe Leu Ile Pro Leu
        450                 455                 460
```

FIG. 6G

```
TCA AAG GTT GAT GAG AAC ATG AAG GTA GCA CAG AAA AGA GAT GCT GTC    1799
Ser Lys Val Asp Glu Asn Met Lys Val Ala Gln Lys Arg Asp Ala Val
465                     470                 475

TTG CAG GGA ATG TTT TAT TTC AGG AAA GAT ATT TGC AAA GGT GGC AAT    1847
Leu Gln Gly Met Phe Tyr Phe Arg Lys Asp Ile Cys Lys Gly Gly Asn
480                 485                 490                 495

GCA GTG GTG GAT GGT TGT GGC AAG GCC CAG AAC AGC ACG GAG CTC GCT    1895
Ala Val Val Asp Gly Cys Gly Lys Ala Gln Asn Ser Thr Glu Leu Ala
        500                 505                 510

GCA GAG GAG TAC ACC CTC ATG AGC ATA GAC ACC ATC AAT GGG AAG        1943
Ala Glu Glu Tyr Thr Leu Met Ser Ile Asp Thr Ile Asn Gly Lys
515                 520                 525

GAA GGT GTG TTT CCT GGA CTG ATC CCA ATT CTG AAC TCT TAC CTT GAA    1991
Glu Gly Val Phe Pro Gly Leu Ile Pro Ile Leu Asn Ser Tyr Leu Glu
        530                 535                 540
```

FIG. 6H

```
AAC ATG GAA GTG GAT GTG GAC ACC AGA TGT AGT ATT CTG AAC TAC CTA    2039
Asn Met Glu Val Asp Val Asp Thr Arg Cys Ser Ile Leu Asn Tyr Leu
    545                 550                 555

AAG CTA ATT AAG AGA GCA TCT GGA GAA CTA ATG ACA GTT GCC AGA        2087
Lys Leu Ile Lys Arg Ala Ser Gly Glu Leu Met Thr Val Ala Arg
    560                 565                 570             575

TGG ATG AGG GAG TTT ATC GCA AAC CAT CCT GAC TAC AAG CAA GAC AGT    2135
Trp Met Arg Glu Phe Ile Ala Asn His Pro Asp Tyr Lys Gln Asp Ser
                580                 585                 590

GTC ATA ACT GAT GAA ATG AAT TAT AGC CTT ATT TTG AAG TGT AAC CAA    2183
Val Ile Thr Asp Glu Met Asn Tyr Ser Leu Ile Leu Lys Cys Asn Gln
            595                 600                 605

ATT GCA AAT GAA TTA TGT GAA TGC CCA GAG TTA CTT GGA TCA GCA TTT    2231
Ile Ala Asn Glu Leu Cys Glu Cys Pro Glu Leu Leu Gly Ser Ala Phe
    610                 615                 620

AGG AAA GTA AAA TAT AGT GGA AGT AAA ACT GAC TCA TCC AAC T          2274
```

FIG. 6I

```
Arg Lys Val Lys Tyr Ser Gly Ser Lys Thr Asp Ser Ser Asn
625                         630                     635
AGACATTCTA CAGAAAGAAA AATGCATTAT TGACGAACTG GCTACAGTAC CATGCCTCTC    2334
AGCCCGTGTG TATAATATGA AGACCAAATG ATAGAACTGT ACTGTTTTCT GGGCCAGTGA    2394
GCCAGAAATT GATTAAGGCT TTCTTTGGTA GGTAAATCTA GAGTTTATAC AGTGTACATG    2454
TACATAGTAA AGTATTTTTG ATTAACAATG TATTTTAATA ACATATCTAA AGTCATCATG    2514
AACTGGCTTG TACATTTTA  AATTCTTACT CTGGAGCAAC CTACTGTCTA AGCAGTTTTG    2574
TAAATGTACT GGTAATTGTA CAATACTTGC ATTCCAGAGT TAAAATGTTT ACTGTAAATT    2634
TTTGTTCTTT TAAAGACTAC CTGGGACCTG ATTTATTGAA ATTTTTCTCT TTAAAAACAT    2694
TTTCTCTCGT TAATTTCCT  TTGTCATTTC CTTTGTTGTC TACATTAAAT CACTTGAATC    2754
CATTGAAAGT GCTTCAAGGG TAATCTTGGG TTTCTAGCAC CTTATCTATG ATGTTTCTTT    2814
TGCAATTGGA ATAATCACTT GGTCACCTTG CCCCAAGCTT TCCCCTCTGA ATAAATACCC    2874
ATTGAACTCT GAAAAAAAAA AAAAAAAA                                       2904
```

FIG. 7A

SEQ. ID. NO. 4

```
Met Gly Leu Leu Ser Gln Gly Ser Pro Leu Ser Trp Glu Glu Thr Lys
 1               5                  10                  15

Arg His Ala Asp His Val Arg Arg His Gly Ile Leu Gln Phe Leu His
                20                  25                  30

Ile Tyr His Ala Val Lys Asp Arg His Lys Asp Val Leu Lys Trp Gly
                35                  40                  45

Asp Glu Val Glu Tyr Met Leu Val Ser Phe Asp His Glu Asn Lys Lys
                50                  55                  60

Val Arg Leu Val Leu Ser Gly Glu Lys Val Leu Glu Thr Leu Gln Glu
65                  70                  75                  80
```

FIG. 7B

Lys Gly Glu Arg Thr Asn Pro Asn His Pro Thr Leu Trp Arg Pro Glu
                 85                  90                  95

Tyr Gly Ser Tyr Met Ile Glu Gly Thr Pro Gly Gln Pro Tyr Gly Gly
            100                 105                 110

Thr Met Ser Glu Phe Asn Thr Val Glu Ala Asn Met Arg Lys Arg Arg
            115                 120                 125

Lys Glu Ala Thr Ser Ile Leu Glu Asn Gln Ala Leu Cys Thr Ile
            130                 135                 140

Thr Ser Phe Pro Arg Leu Gly Cys Pro Gly Phe Thr Leu Pro Glu Val
145                 150                 155                 160

FIG. 7C

Lys Pro Asn Pro Val Glu Gly Gly Ala Ser Lys Ser Leu Phe Phe Pro
                165                            170                      175

Asp Glu Ala Ile Asn Lys His Pro Arg Phe Ser Thr Leu Thr Arg Asn
                180                            185                      190

Ile Arg His Arg Arg Gly Glu Lys Val Val Ile Asn Leu Pro Ile Phe
                195                            200                      205

Lys Asp Lys Asn Thr Pro Ser Pro Phe Ile Glu Thr Phe Thr Glu Asp
                210                            215                      220

Asp Glu Ala Ser Arg Ala Ser Lys Pro Asp His Ile Tyr Met Asp Ala
                225                            230                      235                      240

Met Gly Phe Gly Met Gly Asn Cys Cys Leu Gln Val Thr Phe Gln Ala
                245                            250                      255

Cys Ser Ile Ser Glu Ala Arg Tyr Leu Tyr Asp Gln Leu Ala Thr Ile
                260                            265                      270

Cys Pro Ile Val Met Ala Leu Ser Ala Ala Ser Pro Phe Tyr Arg Gly
                275                            280                      285

FIG. 7D

Tyr Val Ser Asp Ile Asp Cys Arg Trp Gly Val Ile Ser Ala Ser Val
290                    295                    300

Asp Asp Arg Thr Arg Glu Glu Arg Gly Leu Glu Pro Leu Lys Asn Asn
305                    310                    315                    320

Asn Tyr Arg Ile Ser Lys Ser Arg Tyr Asp Ser Ile Asp Ser Tyr Leu
            325                    330                    335

Ser Lys Cys Gly Glu Lys Tyr Asn Asp Ile Asp Leu Thr Ile Asp Lys
            340                    345                    350

Glu Ile Tyr Glu Gln Leu Leu Gln Glu Gly Ile Asp His Leu Leu Ala
            355                    360                    365

Gln His Val Ala His Leu Phe Ile Arg Asp Pro Leu Thr Leu Phe Glu
370                    375                    380

Glu Lys Ile His Leu Asp Asp Ala Asn Glu Ser Asp His Phe Glu Asn
385                    390                    395                    400

FIG. 7E

Ile Gln Ser Thr Asn Trp Gln Thr Met Arg Phe Lys Pro Pro Pro Pro
                405                     410                     415

Asn Ser Asp Ile Gly Trp Arg Val Glu Phe Arg Pro Met Glu Val Gln
                420                     425                     430

Leu Thr Asp Phe Glu Asn Ser Ala Tyr Val Val Phe Val Val Leu Leu
                435                     440                     445

Thr Arg Val Ile Leu Ser Tyr Lys Leu Asp Phe Leu Ile Pro Leu Ser
            450                     455                     460

Lys Val Asp Glu Asn Met Lys Val Ala Gln Lys Arg Asp Ala Val Leu
465                     470                     475                     480

Gln Gly Met Phe Tyr Phe Arg Lys Asp Ile Cys Lys Gly Gly Asn Ala
                485                     490                     495

Val Val Asp Gly Cys Gly Lys Ala Gln Asn Ser Thr Glu Leu Ala Ala

FIG. 7F

```
                               500            505            510
Glu Glu Tyr Thr Leu Met Ser Ile Asp Thr Ile Ile Asn Gly Lys Glu
        515                 520                 525

Gly Val Phe Pro Gly Leu Ile Pro Ile Leu Asn Ser Tyr Leu Glu Asn
        530                 535                 540

Met Glu Val Asp Val Asp Thr Arg Cys Ser Ile Leu Asn Tyr Leu Lys
        545                 550                 555                 560

Leu Ile Lys Lys Arg Ala Ser Gly Glu Leu Met Thr Val Ala Arg Trp
        565                 570                 575

Met Arg Glu Phe Ile Ala Asn His Pro Asp Tyr Lys Gln Asp Ser Val
        580                 585                 590

Ile Thr Asp Glu Met Asn Tyr Ser Leu Ile Leu Lys Cys Asn Gln Ile
        595                 600                 605

Ala Asn Glu Leu Cys Glu Cys Pro Glu Leu Leu Gly Ser Ala Phe Arg
        610                 615                 620

Lys Val Lys Tyr Ser Gly Ser Lys Thr Asp Ser Ser Asn
        625                 630                 635
```

ят5,888,820

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 1842 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: N ( i v ) ANTI-SENSE: N ( v ) FRAGMENT TYPE: N-terminal ( i x ) FEATURE:
      ( A ) NAME/KEY: CDS
      ( B ) LOCATION: 2..1568

( x i ) SEQUENCE DESCRIPTION: SEQ ID NO:1:

```
C  TAG  AAC  CAA  ATT  GCT  GAG  CCA  GTC  ACC  TGT  GTT  CCA  GGA  GCC  GAA           46
   .    Asn  Gln  Ile  Ala  Glu  Pro  Val  Thr  Cys  Val  Pro  Gly  Ala  Glu
        1              5                        10                       15

TCA  GAA  ATG  TCA  TCC  TCA  GGC  ACG  CCA  GAC  TTA  CCT  GTC  CTA  CTC  ACC          94
Ser  Glu  Met  Ser  Ser  Ser  Gly  Thr  Pro  Asp  Leu  Pro  Val  Leu  Leu  Thr
                    20                       25                       30

GAT  TTG  AAG  ATT  CAA  TAT  ACT  AAG  ATC  TTC  ATA  AAC  AAT  GAA  TGG  CAT         142
Asp  Leu  Lys  Ile  Gln  Tyr  Thr  Lys  Ile  Phe  Ile  Asn  Asn  Glu  Trp  His
                    35                       40                       45

GAT  TCA  GTG  AGT  GGC  AAG  AAA  TTT  CCT  GTC  TTT  AAT  CCT  GCA  ACT  GAG         190
Asp  Ser  Val  Ser  Gly  Lys  Lys  Phe  Pro  Val  Phe  Asn  Pro  Ala  Thr  Glu
               50                       55                       60

GAG  GAG  CTC  TGC  CAG  GTA  GAA  GAA  GGA  GAT  AAG  GAG  GAT  GTT  GAC  AAG         238
Glu  Glu  Leu  Cys  Gln  Val  Glu  Glu  Gly  Asp  Lys  Glu  Asp  Val  Asp  Lys
     65                       70                       75

GCA  GTG  AAG  GCC  GCA  AGA  CAG  GCT  TTT  CAG  ATT  GGA  TCT  CCG  TGG  CGT         286
Ala  Val  Lys  Ala  Ala  Arg  Gln  Ala  Phe  Gln  Ile  Gly  Ser  Pro  Trp  Arg
80                       85                       90                       95

ACT  ATG  GAT  GCT  TCC  GAG  AGG  GGG  CGA  CTA  TTA  TAC  AAG  TTG  GCT  GAT         334
Thr  Met  Asp  Ala  Ser  Glu  Arg  Gly  Arg  Leu  Leu  Tyr  Lys  Leu  Ala  Asp
                    100                      105                      110

TTA  ATC  GAA  AGA  GAT  CGT  CTG  CTG  GCG  ACA  ATG  GAG  TCA  ATG  GAG  TCA         382
Leu  Ile  Glu  Arg  Asp  Arg  Leu  Leu  Ala  Thr  Met  Glu  Ser  Met  Glu  Ser
               115                      120                      125

ATG  AAT  GGT  GGA  AAA  CTC  TAT  TCC  AAT  GCA  TAT  CTG  AAT  GAT  TTA  GCA         430
Met  Asn  Gly  Gly  Lys  Leu  Tyr  Ser  Asn  Ala  Tyr  Leu  Asn  Asp  Leu  Ala
          130                      135                      140

GGC  TGC  ATC  AAA  ACA  TTG  CGC  TAC  TGT  GCA  GGT  TGG  GCT  GAC  AAG  ATC         478
Gly  Cys  Ile  Lys  Thr  Leu  Arg  Tyr  Cys  Ala  Gly  Trp  Ala  Asp  Lys  Ile
     145                      150                      155

CAG  GGC  CAG  GGC  CGT  ACA  ATA  CCA  ATT  GAT  GGA  AAT  TTT  TTT  ACA  TAT         526
Gln  Gly  Gln  Gly  Arg  Thr  Ile  Pro  Ile  Asp  Gly  Asn  Phe  Phe  Thr  Tyr
160                      165                      170                      175

ACA  AGA  CAT  GAA  CCT  ATT  GGG  GTA  TGT  GGC  CAA  ATC  ATT  CCT  TGG  AAT         574
Thr  Arg  His  Glu  Pro  Ile  Gly  Val  Cys  Gly  Gln  Ile  Ile  Pro  Trp  Asn
                    180                      185                      190

TTC  CCG  TTG  GTT  ATG  CTC  ATT  TGG  AAG  ATA  GGG  CCT  GCA  CTG  AGC  TGT         622
Phe  Pro  Leu  Val  Met  Leu  Ile  Trp  Lys  Ile  Gly  Pro  Ala  Leu  Ser  Cys
```

|     |     |     |     |     | 195 |     |     |     |     | 200 |     |     |     |     | 205 |      |
|-----|-----|-----|-----|-----|-----|-----|-----|-----|-----|-----|-----|-----|-----|-----|-----|------|

```
GGA  AAC  ACA  GTG  GTT  GTC  AAA  CCA  GCA  GAG  CAA  ACT  CCT  CTC  ACT  GCT       670
Gly  Asn  Thr  Val  Val  Val  Lys  Pro  Ala  Glu  Gln  Thr  Pro  Leu  Thr  Ala
          210                      215                 220

CTC  CAC  GTG  GCA  TCT  TTA  ATA  AAA  GAG  GCA  GGG  TTT  CCT  CCT  GGA  GTA       718
Leu  His  Val  Ala  Ser  Leu  Ile  Lys  Glu  Ala  Gly  Phe  Pro  Pro  Gly  Val
          225                      230                 235

GTG  AAT  ATT  GTT  CCT  GGT  TAT  GGG  CCT  ACA  GCA  GGG  GCA  GCC  ATT  TCT       766
Val  Asn  Ile  Val  Pro  Gly  Tyr  Gly  Pro  Thr  Ala  Gly  Ala  Ala  Ile  Ser
240                           245                 250                           255

TCT  CAC  ATG  GAT  ATA  GAC  AAA  GTA  GCC  TTC  ACA  GGA  TCA  ACA  GAG  GTT       814
Ser  His  Met  Asp  Ile  Asp  Lys  Val  Ala  Phe  Thr  Gly  Ser  Thr  Glu  Val
                    260                      265                      270

GGC  AAG  TTG  ATC  AAA  GAA  GCT  GCC  GGG  AAA  AGC  AAT  CTG  AAG  AGG  GTG       862
Gly  Lys  Leu  Ile  Lys  Glu  Ala  Ala  Gly  Lys  Ser  Asn  Leu  Lys  Arg  Val
                    275                      280                      285

ACC  CTG  GAG  CTT  GGA  GGA  AAG  AGC  CCT  TGC  ATT  GTG  TTA  GCT  GAT  GCC       910
Thr  Leu  Glu  Leu  Gly  Gly  Lys  Ser  Pro  Cys  Ile  Val  Leu  Ala  Asp  Ala
               290                      295                      300

GAC  TTG  GAC  AAT  GCT  GTT  GAA  TTT  GCA  CAC  CAT  GGG  GTA  TTC  TAC  CAC       958
Asp  Leu  Asp  Asn  Ala  Val  Glu  Phe  Ala  His  His  Gly  Val  Phe  Tyr  His
     305                      310                      315

CAG  GGC  CAG  TGT  TGT  ATA  GCC  GCA  TCC  AGG  ATT  TTT  GTG  GAA  GAA  TCA      1006
Gln  Gly  Gln  Cys  Cys  Ile  Ala  Ala  Ser  Arg  Ile  Phe  Val  Glu  Glu  Ser
320                           325                 330                           335

ATT  TAT  GAT  GAG  TTT  GTT  CGA  AGG  AGT  GTT  GAG  CGG  GCT  AAG  AAG  TAT      1054
Ile  Tyr  Asp  Glu  Phe  Val  Arg  Arg  Ser  Val  Glu  Arg  Ala  Lys  Lys  Tyr
                    340                      345                      350

ATC  CTT  GGA  AAT  CCT  CTG  ACC  CCA  GGA  GTC  ACT  CAA  GGC  CCT  CAG  ATT      1102
Ile  Leu  Gly  Asn  Pro  Leu  Thr  Pro  Gly  Val  Thr  Gln  Gly  Pro  Gln  Ile
               355                      360                      365

GAC  AAG  GAA  CAA  TAT  GAT  AAA  ATA  CTT  GAC  CTC  ATT  GAG  AGT  GGG  AAG      1150
Asp  Lys  Glu  Gln  Tyr  Asp  Lys  Ile  Leu  Asp  Leu  Ile  Glu  Ser  Gly  Lys
          370                      375                      380

AAA  GAA  GGG  GCC  AAA  CTG  GAA  TGT  GGA  GGA  GGC  CCG  TGG  GGG  AAT  AAA      1198
Lys  Glu  Gly  Ala  Lys  Leu  Glu  Cys  Gly  Gly  Gly  Pro  Trp  Gly  Asn  Lys
     385                      390                      395

GGC  TAC  TTT  GTC  CAG  CCC  ACA  GTG  TTC  TCT  AAT  GTT  ACA  GAT  GAG  ATG      1246
Gly  Tyr  Phe  Val  Gln  Pro  Thr  Val  Phe  Ser  Asn  Val  Thr  Asp  Glu  Met
400                           405                 410                           415

CGC  ATT  GCC  AAA  GAG  GAG  ATT  TTT  GGA  CCA  GTG  CAG  CAA  ATC  ATG  AAG      1294
Arg  Ile  Ala  Lys  Glu  Glu  Ile  Phe  Gly  Pro  Val  Gln  Gln  Ile  Met  Lys
                    420                      425                      430

TTT  AAA  TCT  TTA  GAT  GAC  GTG  ATC  AAA  AGA  GCA  AAC  AAT  ACT  TTC  TAT      1342
Phe  Lys  Ser  Leu  Asp  Asp  Val  Ile  Lys  Arg  Ala  Asn  Asn  Thr  Phe  Tyr
               435                      440                      445

GGC  TTA  TCA  GCA  GGA  GTG  TTT  ACC  AAA  GAC  ATT  GAT  AAA  GCC  ATA  ACA      1390
Gly  Leu  Ser  Ala  Gly  Val  Phe  Thr  Lys  Asp  Ile  Asp  Lys  Ala  Ile  Thr
          450                      455                      460

ATC  TCC  TCT  GCT  CTG  CAG  GCA  GGA  ACA  GTG  TGG  GTG  AAT  TGC  TAT  GGC      1438
Ile  Ser  Ser  Ala  Leu  Gln  Ala  Gly  Thr  Val  Trp  Val  Asn  Cys  Tyr  Gly
     465                      470                      475

GTG  GTA  AGT  GCC  CAG  TGC  CCC  TTT  GGT  GGA  TTC  AAG  ATG  TCT  GGA  AAT      1486
Val  Val  Ser  Ala  Gln  Cys  Pro  Phe  Gly  Gly  Phe  Lys  Met  Ser  Gly  Asn
480                           485                 490                           495

GGA  AGA  GAA  CTG  GGA  GAG  TAC  GGT  TTC  CAT  GAA  TAT  ACA  GAG  GTC  AAA      1534
Gly  Arg  Glu  Leu  Gly  Glu  Tyr  Gly  Phe  His  Glu  Tyr  Thr  Glu  Val  Lys
                    500                      505                      510

ACA  GTC  ACA  GTG  AAA  ATC  TCT  CAG  AAG  AAC  TCA  T AAAGAAAATA                   1578
Thr  Val  Thr  Val  Lys  Ile  Ser  Gln  Lys  Asn  Ser
```

```
                    5 1 5                         5 2 0
CAAGAGTGGA   GAGAAGCTCT   TCAATAGCTA   AGCATCTCCT   TACAGTCACT   AATATAGTAG    1638

ATTTTAAAGA   CAAAATTTTT   CTTTTCTTGA   TTTTTTTTAA   ACATAAGCTA   AATCATATTA    1698

GTATTAATAC   TACCCATAGA   AAACTTGACA   TGTAGCTTCT   TCTGAAAGAA   TTATTTGCCT    1758

TCTGAAATGT   GACCCCCAAG   TCCTATCCTA   AATAAAAAAA   GACAAATTCG   GATGTATGAT    1818

CTCTCTAGCT   TTGTCATAGT   TATG                                                 1842
```

( 2 ) INFORMATION FOR SEQ ID NO:2:

( i ) SEQUENCE CHARACTERISTICS:
    ( A ) LENGTH: 521 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Asn  Gln  Ile  Ala  Glu  Pro  Val  Thr  Cys  Val  Pro  Gly  Ala  Glu  Ser  Glu
 1                    5                    10                   15

Met  Ser  Ser  Ser  Gly  Thr  Pro  Asp  Leu  Pro  Val  Leu  Leu  Thr  Asp  Leu
               20                        25                       30

Lys  Ile  Gln  Tyr  Thr  Lys  Ile  Phe  Ile  Asn  Asn  Glu  Trp  His  Asp  Ser
          35                        40                        45

Val  Ser  Gly  Lys  Lys  Phe  Pro  Val  Phe  Asn  Pro  Ala  Thr  Glu  Glu  Glu
     50                        55                        60

Leu  Cys  Gln  Val  Glu  Glu  Gly  Asp  Lys  Glu  Asp  Val  Asp  Lys  Ala  Val
 65                       70                        75                        80

Lys  Ala  Ala  Arg  Gln  Ala  Phe  Gln  Ile  Gly  Ser  Pro  Trp  Arg  Thr  Met
                    85                        90                        95

Asp  Ala  Ser  Glu  Arg  Gly  Arg  Leu  Leu  Tyr  Lys  Leu  Ala  Asp  Leu  Ile
               100                       105                       110

Glu  Arg  Asp  Arg  Leu  Leu  Ala  Thr  Met  Glu  Ser  Met  Glu  Ser  Met  Asn
          115                       120                       125

Gly  Gly  Lys  Leu  Tyr  Ser  Asn  Ala  Tyr  Leu  Asn  Asp  Leu  Ala  Gly  Cys
     130                       135                       140

Ile  Lys  Thr  Leu  Arg  Tyr  Cys  Ala  Gly  Trp  Ala  Asp  Lys  Ile  Gln  Gly
145                       150                       155                       160

Gln  Gly  Arg  Thr  Ile  Pro  Ile  Asp  Gly  Asn  Phe  Phe  Thr  Tyr  Thr  Arg
                    165                       170                       175

His  Glu  Pro  Ile  Gly  Val  Cys  Gly  Gln  Ile  Ile  Pro  Trp  Asn  Phe  Pro
               180                       185                       190

Leu  Val  Met  Leu  Ile  Trp  Lys  Ile  Gly  Pro  Ala  Leu  Ser  Cys  Gly  Asn
          195                       200                       205

Thr  Val  Val  Val  Lys  Pro  Ala  Glu  Gln  Thr  Pro  Leu  Thr  Ala  Leu  His
     210                       215                       220

Val  Ala  Ser  Leu  Ile  Lys  Glu  Ala  Gly  Phe  Pro  Pro  Gly  Val  Val  Asn
225                       230                       235                       240

Ile  Val  Pro  Gly  Tyr  Gly  Pro  Thr  Ala  Gly  Ala  Ala  Ile  Ser  Ser  His
                    245                       250                       255

Met  Asp  Ile  Asp  Lys  Val  Ala  Phe  Thr  Gly  Ser  Thr  Glu  Val  Gly  Lys
               260                       265                       270

Leu  Ile  Lys  Glu  Ala  Ala  Gly  Lys  Ser  Asn  Leu  Lys  Arg  Val  Thr  Leu
          275                       280                       285

Glu  Leu  Gly  Gly  Lys  Ser  Pro  Cys  Ile  Val  Leu  Ala  Asp  Ala  Asp  Leu
     290                       295                       300
```

| | | | | | | | | | | | | | | | |
|---|---|---|---|---|---|---|---|---|---|---|---|---|---|---|---|
| Asp | Asn | Ala | Val | Glu | Phe | Ala | His | His | Gly | Val | Phe | Tyr | His | Gln | Gly |
| 305 | | | | 310 | | | | | 315 | | | | | | 320 |
| Gln | Cys | Cys | Ile | Ala | Ala | Ser | Arg | Ile | Phe | Val | Glu | Glu | Ser | Ile | Tyr |
| | | | | 325 | | | | | 330 | | | | | 335 | |
| Asp | Glu | Phe | Val | Arg | Arg | Ser | Val | Glu | Arg | Ala | Lys | Lys | Tyr | Ile | Leu |
| | | | 340 | | | | | 345 | | | | | 350 | | |
| Gly | Asn | Pro | Leu | Thr | Pro | Gly | Val | Thr | Gln | Gly | Pro | Gln | Ile | Asp | Lys |
| | | 355 | | | | | 360 | | | | | 365 | | | |
| Glu | Gln | Tyr | Asp | Lys | Ile | Leu | Asp | Leu | Ile | Glu | Ser | Gly | Lys | Lys | Glu |
| | 370 | | | | | 375 | | | | | 380 | | | | |
| Gly | Ala | Lys | Leu | Glu | Cys | Gly | Gly | Gly | Pro | Trp | Gly | Asn | Lys | Gly | Tyr |
| 385 | | | | | 390 | | | | | 395 | | | | | 400 |
| Phe | Val | Gln | Pro | Thr | Val | Phe | Ser | Asn | Val | Thr | Asp | Glu | Met | Arg | Ile |
| | | | | 405 | | | | | 410 | | | | | 415 | |
| Ala | Lys | Glu | Glu | Ile | Phe | Gly | Pro | Val | Gln | Gln | Ile | Met | Lys | Phe | Lys |
| | | | 420 | | | | | 425 | | | | | 430 | | |
| Ser | Leu | Asp | Asp | Val | Ile | Lys | Arg | Ala | Asn | Asn | Thr | Phe | Tyr | Gly | Leu |
| | | 435 | | | | | 440 | | | | | 445 | | | |
| Ser | Ala | Gly | Val | Phe | Thr | Lys | Asp | Ile | Asp | Lys | Ala | Ile | Thr | Ile | Ser |
| | 450 | | | | | 455 | | | | | 460 | | | | |
| Ser | Ala | Leu | Gln | Ala | Gly | Thr | Val | Trp | Val | Asn | Cys | Tyr | Gly | Val | Val |
| 465 | | | | | 470 | | | | | 475 | | | | | 480 |
| Ser | Ala | Gln | Cys | Pro | Phe | Gly | Gly | Phe | Lys | Met | Ser | Gly | Asn | Gly | Arg |
| | | | | 485 | | | | | 490 | | | | | 495 | |
| Glu | Leu | Gly | Glu | Tyr | Gly | Phe | His | Glu | Tyr | Thr | Glu | Val | Lys | Thr | Val |
| | | | 500 | | | | | 505 | | | | | 510 | | |
| Thr | Val | Lys | Ile | Ser | Gln | Lys | Asn | Ser | | | | | | | |
| | | 515 | | | | | 520 | | | | | | | | |

( 2 ) INFORMATION FOR SEQ ID NO:3:

( i ) SEQUENCE CHARACTERISTICS:
        ( A ) LENGTH: 2904 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( v ) FRAGMENT TYPE: N-terminal ( i x ) FEATURE:
        ( A ) NAME/KEY: CDS
        ( B ) LOCATION: 363..2274
        ( D ) OTHER INFORMATION:

( x i ) SEQUENCE DESCRIPTION: SEQ ID NO:3:

```
GAATTCCGGG  CGGGAGCCGC  CGCGGCAGCG  CGGCCGTGGG  GTCCGCCGCC  GCCGCATCGG        60
AGCGGGAGGA  GGAGCAGCGG  GGAGGGCGAG  GCCGCCGGGC  CGAGAGCCGT  CCCGCCTGCT       120
CTCGGTCTTC  TGCCTTCGCC  TCCGCGCGGT  GCGTCGGACC  CAGGGTCTGT  CACCTGGGCG       180
CCAGGGGCCG  CCGCCGGGGA  GCCGGAGCGG  GCAGGACCCT  CCCTCCGCCG  ACTGCGGCCC       240
GAGAGCGCCC  CCGCGGGGTG  GAGCGGCAGC  CGCCTTCTGC  GGGCGGCTGA  GTGTCCGTCT       300
CGCGCCCGGA  GCGGGCGACC  GCCGTCAGCC  CGGAGGAGGA  GGAGGAGGAG  GAGGGGGCGT       360
CC ATG GGG CTG CTG TCC CAG GGC TCG CCG CTG AGC TGG GAG GAA ACC              407
```

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Gly | Leu | Leu | Ser | Gln | Gly | Ser | Pro | Leu | Ser | Trp | Glu | Glu | Thr | |
| 1   |     |     |     | 5   |     |     |     |     | 10  |     |     |     |     | 15  | |

| AAG | CGC | CAT | GCC | GAC | CAC | GTG | CGG | CGG | CAC | GGG | ATC | CTC | CAG | TTC | CTG | 455 |
| Lys | Arg | His | Ala | Asp | His | Val | Arg | Arg | His | Gly | Ile | Leu | Gln | Phe | Leu | |
|     |     |     | 20  |     |     |     |     | 25  |     |     |     |     | 30  |     |     | |

| CAC | ATC | TAC | CAC | GCC | GTC | AAG | GAC | CGG | CAC | AAG | GAC | GTT | CTC | AAG | TGG | 503 |
| His | Ile | Tyr | His | Ala | Val | Lys | Asp | Arg | His | Lys | Asp | Val | Leu | Lys | Trp | |
|     |     |     | 35  |     |     |     |     | 40  |     |     |     |     | 45  |     |     | |

| GGC | GAT | GAG | GTG | GAA | TAC | ATG | TTG | GTA | TCT | TTT | GAT | CAT | GAA | AAT | AAA | 551 |
| Gly | Asp | Glu | Val | Glu | Tyr | Met | Leu | Val | Ser | Phe | Asp | His | Glu | Asn | Lys | |
|     |     |     | 50  |     |     |     |     | 55  |     |     |     |     | 60  |     |     | |

| AAA | GTC | CGG | TTG | GTC | CTG | TCT | GGG | GAG | AAA | GTT | CTT | GAA | ACT | CTG | CAA | 599 |
| Lys | Val | Arg | Leu | Val | Leu | Ser | Gly | Glu | Lys | Val | Leu | Glu | Thr | Leu | Gln | |
|     |     |     | 65  |     |     |     |     | 70  |     |     |     |     | 75  |     |     | |

| GAG | AAG | GGG | GAA | AGG | ACA | AAC | CCA | AAC | CAT | CCT | ACC | CTT | TGG | AGA | CCA | 647 |
| Glu | Lys | Gly | Glu | Arg | Thr | Asn | Pro | Asn | His | Pro | Thr | Leu | Trp | Arg | Pro | |
| 80  |     |     |     |     | 85  |     |     |     |     | 90  |     |     |     |     | 95  | |

| GAG | TAT | GGG | AGT | TAC | ATG | ATT | GAA | GGG | ACA | CCA | GGA | CAG | CCC | TAC | GGA | 695 |
| Glu | Tyr | Gly | Ser | Tyr | Met | Ile | Glu | Gly | Thr | Pro | Gly | Gln | Pro | Tyr | Gly | |
|     |     |     |     | 100 |     |     |     |     | 105 |     |     |     |     | 110 |     | |

| GGA | ACA | ATG | TCC | GAG | TTC | AAT | ACA | GTT | GAG | GCC | AAC | ATG | CGA | AAA | CGC | 743 |
| Gly | Thr | Met | Ser | Glu | Phe | Asn | Thr | Val | Glu | Ala | Asn | Met | Arg | Lys | Arg | |
|     |     |     | 115 |     |     |     |     | 120 |     |     |     |     | 125 |     |     | |

| CGG | AAG | GAG | GCT | ACT | TCT | ATA | TTA | GAA | GAA | AAT | CAG | GCT | CTT | TGC | ACA | 791 |
| Arg | Lys | Glu | Ala | Thr | Ser | Ile | Leu | Glu | Glu | Asn | Gln | Ala | Leu | Cys | Thr | |
|     |     | 130 |     |     |     |     | 135 |     |     |     |     | 140 |     |     |     | |

| ATA | ACT | TCA | TTT | CCC | AGA | TTA | GGC | TGT | CCT | GGG | TTC | ACA | CTG | CCC | GAG | 839 |
| Ile | Thr | Ser | Phe | Pro | Arg | Leu | Gly | Cys | Pro | Gly | Phe | Thr | Leu | Pro | Glu | |
|     |     | 145 |     |     |     |     | 150 |     |     |     |     | 155 |     |     |     | |

| GTC | AAA | CCC | AAC | CCA | GTG | GAA | GGA | GGA | GCT | TCC | AAG | TCC | CTC | TTC | TTT | 887 |
| Val | Lys | Pro | Asn | Pro | Val | Glu | Gly | Gly | Ala | Ser | Lys | Ser | Leu | Phe | Phe | |
| 160 |     |     |     |     | 165 |     |     |     |     | 170 |     |     |     |     | 175 | |

| CCA | GAT | GAA | GCA | ATA | AAC | AAG | CAC | CCT | CGC | TTC | AGT | ACC | TTA | ACA | AGA | 935 |
| Pro | Asp | Glu | Ala | Ile | Asn | Lys | His | Pro | Arg | Phe | Ser | Thr | Leu | Thr | Arg | |
|     |     |     |     | 180 |     |     |     |     | 185 |     |     |     |     | 190 |     | |

| AAT | ATC | CGA | CAT | AGG | AGA | GGA | GAA | AAG | GTT | GTC | ATC | AAT | GTA | CCA | ATA | 983 |
| Asn | Ile | Arg | His | Arg | Arg | Gly | Glu | Lys | Val | Val | Ile | Asn | Val | Pro | Ile | |
|     |     |     | 195 |     |     |     |     | 200 |     |     |     |     | 205 |     |     | |

| TTT | AAG | GAC | AAG | AAT | ACA | CCA | TCT | CCA | TTT | ATA | GAA | ACA | TTT | ACT | GAG | 1031 |
| Phe | Lys | Asp | Lys | Asn | Thr | Pro | Ser | Pro | Phe | Ile | Glu | Thr | Phe | Thr | Glu | |
|     |     |     | 210 |     |     |     |     | 215 |     |     |     |     | 220 |     |     | |

| GAT | GAT | GAA | GCT | TCA | AGG | GCT | TCT | AAG | CCG | GAT | CAT | ATT | TAC | ATG | GAT | 1079 |
| Asp | Asp | Glu | Ala | Ser | Arg | Ala | Ser | Lys | Pro | Asp | His | Ile | Tyr | Met | Asp | |
|     |     | 225 |     |     |     |     | 230 |     |     |     |     | 235 |     |     |     | |

| GCC | ATG | GGA | TTT | GGA | ATG | GGC | AAT | TGC | TGT | CTC | CAG | GTG | ACA | TTC | CAA | 1127 |
| Ala | Met | Gly | Phe | Gly | Met | Gly | Asn | Cys | Cys | Leu | Gln | Val | Thr | Phe | Gln | |
| 240 |     |     |     |     | 245 |     |     |     |     | 250 |     |     |     |     | 255 | |

| GCC | TGC | AGT | ATA | TCT | GAG | GCC | AGA | TAC | CTT | TAT | GAT | CAG | TTG | GCT | ACT | 1175 |
| Ala | Cys | Ser | Ile | Ser | Glu | Ala | Arg | Tyr | Leu | Tyr | Asp | Gln | Leu | Ala | Thr | |
|     |     |     |     | 260 |     |     |     |     | 265 |     |     |     |     | 270 |     | |

| ATC | TGT | CCA | ATT | GTT | ATG | GCT | TTG | AGT | GCT | GCA | TCT | CCC | TTT | TAC | CGA | 1223 |
| Ile | Cys | Pro | Ile | Val | Met | Ala | Leu | Ser | Ala | Ala | Ser | Pro | Phe | Tyr | Arg | |
|     |     |     | 275 |     |     |     |     | 280 |     |     |     |     | 285 |     |     | |

| GGC | TAT | GTG | TCA | GAC | ATT | GAT | TGT | CGC | TGG | GGA | GTG | ATT | TCT | GCA | TCT | 1271 |
| Gly | Tyr | Val | Ser | Asp | Ile | Asp | Cys | Arg | Trp | Gly | Val | Ile | Ser | Ala | Ser | |
|     |     |     | 290 |     |     |     |     | 295 |     |     |     |     | 300 |     |     | |

| GTA | GAT | GAT | AGA | ACT | CGG | GAG | GAG | CGA | GGA | CTG | GAG | CCA | TTG | AAG | AAC | 1319 |
| Val | Asp | Asp | Arg | Thr | Arg | Glu | Glu | Arg | Gly | Leu | Glu | Pro | Leu | Lys | Asn | |
|     |     | 305 |     |     |     |     | 310 |     |     |     |     | 315 |     |     |     | |

| AAT | AAC | TAT | AGG | ATC | AGT | AAA | TCC | CGA | TAT | GAC | TCA | ATA | GAC | AGC | TAT | 1367 |

```
Asn  Asn  Tyr  Arg  Ile  Ser  Lys  Ser  Arg  Tyr  Asp  Ser  Ile  Asp  Ser  Tyr
320            325                 330                 335

TTA  TCT  AAG  TGT  GGT  GAG  AAA  TAT  AAT  GAC  ATC  GAC  TTG  ACG  ATA  GAT        1415
Leu  Ser  Lys  Cys  Gly  Glu  Lys  Tyr  Asn  Asp  Ile  Asp  Leu  Thr  Ile  Asp
               340                 345                      350

AAA  GAG  ATC  TAC  GAA  CAG  CTG  TTG  CAG  GAA  GGC  ATT  GAT  CAT  CTC  CTG        1463
Lys  Glu  Ile  Tyr  Glu  Gln  Leu  Leu  Gln  Glu  Gly  Ile  Asp  His  Leu  Leu
               355                 360                      365

GCC  CAG  CAT  GTT  GCT  CAT  CTC  TTT  ATT  AGA  GAC  CCA  CTG  ACA  CTG  TTT        1511
Ala  Gln  His  Val  Ala  His  Leu  Phe  Ile  Arg  Asp  Pro  Leu  Thr  Leu  Phe
          370                 375                      380

GAA  GAG  AAA  ATA  CAC  CTG  GAT  GAT  GCT  AAT  GAG  TCT  GAC  CAT  TTT  GAG        1559
Glu  Glu  Lys  Ile  His  Leu  Asp  Asp  Ala  Asn  Glu  Ser  Asp  His  Phe  Glu
          385                 390                      395

AAT  ATT  CAG  TCC  ACA  AAT  TGG  CAG  ACA  ATG  AGA  TTT  AAG  CCC  CCT  CCT        1607
Asn  Ile  Gln  Ser  Thr  Asn  Trp  Gln  Thr  Met  Arg  Phe  Lys  Pro  Pro  Pro
400                 405                 410                           415

CCA  AAC  TCA  GAC  ATT  GGA  TGG  AGA  GTA  GAA  TTT  CGA  CCC  ATG  GAG  GTG        1655
Pro  Asn  Ser  Asp  Ile  Gly  Trp  Arg  Val  Glu  Phe  Arg  Pro  Met  Glu  Val
               420                 425                      430

CAA  TTA  ACA  GAC  TTT  GAG  AAC  TCT  GCC  TAT  GTG  GTG  TTT  GTG  GTA  CTG        1703
Gln  Leu  Thr  Asp  Phe  Glu  Asn  Ser  Ala  Tyr  Val  Val  Phe  Val  Val  Leu
               435                 440                      445

CTC  ACC  AGA  GTG  ATC  CTT  TCC  TAC  AAA  TTG  GAT  TTT  CTC  ATT  CCA  CTG        1751
Leu  Thr  Arg  Val  Ile  Leu  Ser  Tyr  Lys  Leu  Asp  Phe  Leu  Ile  Pro  Leu
          450                 455                      460

TCA  AAG  GTT  GAT  GAG  AAC  ATG  AAG  GTA  GCA  CAG  AAA  AGA  GAT  GCT  GTC        1799
Ser  Lys  Val  Asp  Glu  Asn  Met  Lys  Val  Ala  Gln  Lys  Arg  Asp  Ala  Val
     465                      470                 475

TTG  CAG  GGA  ATG  TTT  TAT  TTC  AGG  AAA  GAT  ATT  TGC  AAA  GGT  GGC  AAT        1847
Leu  Gln  Gly  Met  Phe  Tyr  Phe  Arg  Lys  Asp  Ile  Cys  Lys  Gly  Gly  Asn
480                 485                 490                           495

GCA  GTG  GTG  GAT  GGT  TGT  GGC  AAG  GCC  CAG  AAC  AGC  ACG  GAG  CTC  GCT        1895
Ala  Val  Val  Asp  Gly  Cys  Gly  Lys  Ala  Gln  Asn  Ser  Thr  Glu  Leu  Ala
               500                 505                      510

GCA  GAG  GAG  TAC  ACC  CTC  ATG  AGC  ATA  GAC  ACC  ATC  ATC  AAT  GGG  AAG        1943
Ala  Glu  Glu  Tyr  Thr  Leu  Met  Ser  Ile  Asp  Thr  Ile  Ile  Asn  Gly  Lys
               515                 520                      525

GAA  GGT  GTG  TTT  CCT  GGA  CTG  ATC  CCA  ATT  CTG  AAC  TCT  TAC  CTT  GAA        1991
Glu  Gly  Val  Phe  Pro  Gly  Leu  Ile  Pro  Ile  Leu  Asn  Ser  Tyr  Leu  Glu
          530                 535                      540

AAC  ATG  GAA  GTG  GAT  GTG  GAC  ACC  AGA  TGT  AGT  ATT  CTG  AAC  TAC  CTA        2039
Asn  Met  Glu  Val  Asp  Val  Asp  Thr  Arg  Cys  Ser  Ile  Leu  Asn  Tyr  Leu
545                 550                 555

AAG  CTA  ATT  AAG  AAG  AGA  GCA  TCT  GGA  GAA  CTA  ATG  ACA  GTT  GCC  AGA        2087
Lys  Leu  Ile  Lys  Lys  Arg  Ala  Ser  Gly  Glu  Leu  Met  Thr  Val  Ala  Arg
560                 565                 570                           575

TGG  ATG  AGG  GAG  TTT  ATC  GCA  AAC  CAT  CCT  GAC  TAC  AAG  CAA  GAC  AGT        2135
Trp  Met  Arg  Glu  Phe  Ile  Ala  Asn  His  Pro  Asp  Tyr  Lys  Gln  Asp  Ser
               580                 585                      590

GTC  ATA  ACT  GAT  GAA  ATG  AAT  TAT  AGC  CTT  ATT  TTG  AAG  TGT  AAC  CAA        2183
Val  Ile  Thr  Asp  Glu  Met  Asn  Tyr  Ser  Leu  Ile  Leu  Lys  Cys  Asn  Gln
               595                 600                      605

ATT  GCA  AAT  GAA  TTA  TGT  GAA  TGC  CCA  GAG  TTA  CTT  GGA  TCA  GCA  TTT        2231
Ile  Ala  Asn  Glu  Leu  Cys  Glu  Cys  Pro  Glu  Leu  Leu  Gly  Ser  Ala  Phe
          610                 615                      620

AGG  AAA  GTA  AAA  TAT  AGT  GGA  AGT  AAA  ACT  GAC  TCA  TCC  AAC  T                2274
Arg  Lys  Val  Lys  Tyr  Ser  Gly  Ser  Lys  Thr  Asp  Ser  Ser  Asn
          625                 630                      635

AGACATTCTA CAGAAAGAAA AATGCATTAT TGACGAACTG GCTACAGTAC CATGCCTCTC                     2334
```

```
AGCCCGTGTG  TATAATATGA  AGACCAAATG  ATAGAACTGT  ACTGTTTTCT  GGGCCAGTGA    2394

GCCAGAAATT  GATTAAGGCT  TTCTTTGGTA  GGTAAATCTA  GAGTTTATAC  AGTGTACATG    2454

TACATAGTAA  AGTATTTTTG  ATTAACAATG  TATTTTAATA  ACATATCTAA  AGTCATCATG    2514

AACTGGCTTG  TACATTTTTA  AATTCTTACT  CTGGAGCAAC  CTACTGTCTA  AGCAGTTTTG    2574

TAAATGTACT  GGTAATTGTA  CAATACTTGC  ATTCCAGAGT  TAAAATGTTT  ACTGTAAATT    2634

TTTGTTCTTT  TAAAGACTAC  CTGGGACCTG  ATTTATTGAA  ATTTTTCTCT  TTAAAAACAT    2694

TTTCTCTCGT  TAATTTTCCT  TTGTCATTTC  CTTTGTTGTC  TACATTAAAT  CACTTGAATC    2754

CATTGAAAGT  GCTTCAAGGG  TAATCTTGGG  TTTCTAGCAC  CTTATCTATG  ATGTTTCTTT    2814

TGCAATTGGA  ATAATCACTT  GGTCACCTTG  CCCCAAGCTT  TCCCCTCTGA  ATAAATACCC    2874

ATTGAACTCT  GAAAAAAAAA  AAAAAAAAA                                        2904
```

( 2 ) INFORMATION FOR SEQ ID NO:4:

( i ) SEQUENCE CHARACTERISTICS:
        ( A ) LENGTH: 637 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Gly  Leu  Leu  Ser  Gln  Gly  Ser  Pro  Leu  Ser  Trp  Glu  Glu  Thr  Lys
 1              5                        10                       15

Arg  His  Ala  Asp  His  Val  Arg  Arg  His  Gly  Ile  Leu  Gln  Phe  Leu  His
               20                        25                       30

Ile  Tyr  His  Ala  Val  Lys  Asp  Arg  His  Lys  Asp  Val  Leu  Lys  Trp  Gly
          35                        40                       45

Asp  Glu  Val  Glu  Tyr  Met  Leu  Val  Ser  Phe  Asp  His  Glu  Asn  Lys  Lys
     50                        55                       60

Val  Arg  Leu  Val  Leu  Ser  Gly  Lys  Val  Leu  Glu  Thr  Leu  Gln  Glu
65                        70                       75                       80

Lys  Gly  Glu  Arg  Thr  Asn  Pro  Asn  His  Pro  Thr  Leu  Trp  Arg  Pro  Glu
                    85                       90                       95

Tyr  Gly  Ser  Tyr  Met  Ile  Glu  Gly  Thr  Pro  Gly  Gln  Pro  Tyr  Gly  Gly
               100                       105                       110

Thr  Met  Ser  Glu  Phe  Asn  Thr  Val  Glu  Ala  Asn  Met  Arg  Lys  Arg  Arg
          115                       120                       125

Lys  Glu  Ala  Thr  Ser  Ile  Leu  Glu  Glu  Asn  Gln  Ala  Leu  Cys  Thr  Ile
     130                       135                       140

Thr  Ser  Phe  Pro  Arg  Leu  Gly  Cys  Pro  Gly  Phe  Thr  Leu  Pro  Glu  Val
145                       150                       155                       160

Lys  Pro  Asn  Pro  Val  Glu  Gly  Gly  Ala  Ser  Lys  Ser  Leu  Phe  Phe  Pro
                    165                       170                       175

Asp  Glu  Ala  Ile  Asn  Lys  His  Pro  Arg  Phe  Ser  Thr  Leu  Thr  Arg  Asn
               180                       185                       190

Ile  Arg  His  Arg  Arg  Gly  Glu  Lys  Val  Val  Ile  Asn  Val  Pro  Ile  Phe
          195                       200                       205

Lys  Asp  Lys  Asn  Thr  Pro  Ser  Pro  Phe  Ile  Glu  Thr  Phe  Thr  Glu  Asp
     210                       215                       220

Asp  Glu  Ala  Ser  Arg  Ala  Ser  Lys  Pro  Asp  His  Ile  Tyr  Met  Asp  Ala
225                       230                       235                       240

Met  Gly  Phe  Gly  Met  Gly  Asn  Cys  Cys  Leu  Gln  Val  Thr  Phe  Gln  Ala
                    245                       250                       255
```

```
Cys Ser Ile Ser Glu Ala Arg Tyr Leu Tyr Asp Gln Leu Ala Thr Ile
            260                 265                 270
Cys Pro Ile Val Met Ala Leu Ser Ala Ala Ser Pro Phe Tyr Arg Gly
        275                 280             285
Tyr Val Ser Asp Ile Asp Cys Arg Trp Gly Val Ile Ser Ala Ser Val
    290             295                 300
Asp Asp Arg Thr Arg Glu Glu Arg Gly Leu Glu Pro Leu Lys Asn Asn
305                 310                 315                 320
Asn Tyr Arg Ile Ser Lys Ser Arg Tyr Asp Ser Ile Asp Ser Tyr Leu
                325                 330                 335
Ser Lys Cys Gly Glu Lys Tyr Asn Asp Ile Asp Leu Thr Ile Asp Lys
            340                 345                 350
Glu Ile Tyr Glu Gln Leu Leu Gln Glu Gly Ile Asp His Leu Leu Ala
        355                 360                 365
Gln His Val Ala His Leu Phe Ile Arg Asp Pro Leu Thr Leu Phe Glu
    370                 375                 380
Glu Lys Ile His Leu Asp Asp Ala Asn Glu Ser Asp His Phe Glu Asn
385                 390                 395                 400
Ile Gln Ser Thr Asn Trp Gln Thr Met Arg Phe Lys Pro Pro Pro Pro
                405                 410                 415
Asn Ser Asp Ile Gly Trp Arg Val Glu Phe Arg Pro Met Glu Val Gln
            420                 425                 430
Leu Thr Asp Phe Glu Asn Ser Ala Tyr Val Val Phe Val Val Leu Leu
        435                 440                 445
Thr Arg Val Ile Leu Ser Tyr Lys Leu Asp Phe Leu Ile Pro Leu Ser
    450                 455                 460
Lys Val Asp Glu Asn Met Lys Val Ala Gln Lys Arg Asp Ala Val Leu
465                 470                 475                 480
Gln Gly Met Phe Tyr Phe Arg Lys Asp Ile Cys Lys Gly Gly Asn Ala
                485                 490                 495
Val Val Asp Gly Cys Gly Lys Ala Gln Asn Ser Thr Glu Leu Ala Ala
            500                 505                 510
Glu Glu Tyr Thr Leu Met Ser Ile Asp Thr Ile Ile Asn Gly Lys Glu
        515                 520                 525
Gly Val Phe Pro Gly Leu Ile Pro Ile Leu Asn Ser Tyr Leu Glu Asn
    530                 535                 540
Met Glu Val Asp Val Asp Thr Arg Cys Ser Ile Leu Asn Tyr Leu Lys
545                 550                 555                 560
Leu Ile Lys Lys Arg Ala Ser Gly Glu Leu Met Thr Val Ala Arg Trp
                565                 570                 575
Met Arg Glu Phe Ile Ala Asn His Pro Asp Tyr Lys Gln Asp Ser Val
            580                 585                 590
Ile Thr Asp Glu Met Asn Tyr Ser Leu Ile Leu Lys Cys Asn Gln Ile
        595                 600                 605
Ala Asn Glu Leu Cys Glu Cys Pro Glu Leu Leu Gly Ser Ala Phe Arg
    610                 615                 620
Lys Val Lys Tyr Ser Gly Ser Lys Thr Asp Ser Ser Asn
625                 630                 635
```

RETROVIRAL VECTOR CAPABLE OF TRANSDUCING THE ALDEHYDE DEHYDROGENASE-1 GENE AND USES OF SAID VECTOR

This application is a 371 of PCT 1 US94/03624 filed on Apr. 1, 1994 and a continuation-in-part of U.S. application Ser. No. 08/041,722, filed on Apr. 1, 1993, now abandoned, the contents of which are hereby incorporated by reference.

Throughout this application various publications are referenced by the names of the authors and the year of the publication within parentheses. Full citations for these publications may be found at the end of the specification immediately preceding the claims. The disclosures of these publications in their entireties are hereby incorporated by reference into this application in order to more fully describe the state of the art to which this invention pertains.

BACKGROUND OF INVENTION

Recent advances in autologous bone marrow transplant strategies indicate that normal hematopoiesis can be promptly restored in patients treated with myelotoxic agents (drugs or radiation) by re-injection of autologous peripheral blood (CD34$^+$) "stem cells" (Gianni, et al., Lancet 2:580, 1989). In addition, it has very recently been reported that CD34$^+$ cells can be transduced in vitro at high efficiency with retroviral vectors expressing specific genes (Bregni, et al., Blood 80:1418, 1992). These technologies open the way to approaches in which the in vitro transduction of specific genes into autologous CD34$^+$ cells followed by reinoculation into patients can be used to transduce genes of therapeutic significance. This gene therapy approach includes the reconstitution of drug-resistant hematopoietic cells allowing for subsequent treatment with higher dose myelotoxic chemotherapy in cancer patients.

SUMMARY OF INVENTION

This invention provides a vector which comprises a nucleic acid molecule encoding a human cytosolic aldehyde dehydrogenase.

In addition, this invention provides a vector which comprises a nucleic acid molecule encoding a human glutamylcysteine synthetase.

In addition, this invention provides a retroviral vector, which comprises a nucleic acid molecule encoding a human cytosolic aldehyde dehydrogenase.

In addition, this invention provides a retroviral vector, which comprises a nucleic acid molecule encoding a human glutamylcysteine synthetase.

In addition, this invention provides a vector, which comprises a nucleic acid molecule encoding a human cytosolic aldehyde dehydrogenase and a glutamylcysteine synthetase.

In addition, this invention provides a method for reducing the toxic effects of a cyclophosphamide in a subject which comprises replacing the subject's hematopoietic cells with hematopoietic cells of having the retroviral vector which comprises a nucleic acid molecule encoding a human cytosolic aldehyde dehydrogenase so as to reduce the toxic effects of the cyclophosphamide in the subject.

In addition, this invention provides a method for introducing a selectable marker into a mammalian cell which comprises transfecting the cell with a nucleic acid molecule encoding human cytosolic aldehyde dehydrogenase.

In addition, this invention provides a method for selecting mammalian cells expressing a protein of interest which comprises: a) introducing into the cells a nucleic acid molecule comprising a nucleic acid molecule encoding the protein of interest and the nucleic acid molecule encoding human cytosolic aldehyde dehydrogenase; b) culturing the resulting transfected cells; and c) selecting cells which express human cytosolic aldehyde dehydrogenase, so as to obtain cells which express the protein of interest.

In addition, this invention provides a method for reducing the toxic effects of a cyclophosphamide in a subject which comprises replacing the subject's hematopoietic cells with hematopoietic cells of having the retroviral vector which comprises a nucleic acid molecule encoding a human glutamylcysteine synthetase so as to reduce the toxic effects of the cyclophosphamide in the subject.

In addition, this invention provides a method for introducing a selectable marker into a mammalian cell which comprises transfecting the cell with a nucleic acid molecule encoding human glutamylcysteine synthetase.

In addition, this invention provides a method for selecting mammalian cells expressing a protein of interest which comprises: a) introducing into the cells a nucleic acid molecule comprising a nucleic acid molecule encoding the protein of interest and the nucleic acid molecule encoding human glutamylcysteine synthetase; b) culturing the resulting transfected cells; and c) selecting cells which express human glutamylcysteine synthetase, so as to obtain cells which express the protein of interest.

In addition, this invention provides an isolated mammalian nucleic acid molecule encoding a cytosolic aldehyde dehydrogenase. The isolated mammalian nucleic acid molecule may have substantially the same sequence shown in FIGS. 4A–4G (SEQ ID NO: 1).

In addition, this invention provides an isolated mammalian nucleic acid molecule encoding a glutamylcysteine synthetase. The isolated mammalian nucleic acid molecule may have substantially the same sequence shown in FIG. 6 (SEQ ID NO: 3).

In addition, this invention provides a nucleic acid molecule of at least 15 nucleotides capable of specifically hybridizing with a sequence of the nucleic acid molecule of the isolated mammalian nucleic acid molecule encoding an cytosolic aldehyde dehydrogenase or a glutamylcysteine synthetase.

In addition, this invention provides a method of detecting expression of an aldehyde dehydrogenase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian cytosolic aldehyde dehydrogenase which comprises growing the host cells of the host vector system under suitable conditions permitting production of the polypeptide and recovering the polypeptide so produced.

In addition, this invention provides a method of detecting expression of a glutamylcysteine synthetase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian glutamylcysteine synthetase which comprises growing the host cells of the host vector system under suitable conditions permitting production of the polypeptide and recovering the polypeptide so produced.

In addition, this invention provides an antibody directed against an amino acid molecule of a cytosolic aldehyde dehydrogenase.

In addition, this invention provides an antibody directed against an amino acid molecule of a glutamylcysteine synthetase.

In addition, this invention provides an immunoassay for measuring the amount of a mammalian cytosolic aldehyde dehydrogenase in a biological sample comprising steps of: a) contacting the biological sample with at least one antibody, either monoclonal or ployclonal, to form a complex with said antibody and the cytosolic aldehyde dehydrogenase, and b) measuring the amount of the cytosolic aldehyde dehydrogenase in said biological sample by measuring the amount of said complex.

In addition, this invention provides a transgenic nonhuman mammal which comprises the isolated mammalian nucleic acid molecule encoding an cytosolic aldehyde dehydrogenase or a glutamylcysteine synthetase.

In addition, this invention provides a transgenic nonhuman mammal whose genome comprises antisense DNA complementary to DNA encoding a cytosolic aldehyde dehydrogenase so placed as to be transcribed into antisense mRNA complementary to mRNA encoding the cytosolic aldehyde dehydrogenase and which hybridizes to mRNA encoding the mammalian cytosolic aldehyde dehydrogenase thereby reducing its translation.

In addition, this invention provides a transgenic nonhuman mammal whose genome comprises antisense DNA complementary to DNA encoding a glutamylcysteine synthetase so placed as to be transcribed into antisense mRNA complementary to mRNA encoding the glutamylcysteine synthetase and which hybridizes to mRNA encoding the mammalian glutamylcyseine synthetase thereby reducing its translation.

In addition, this invention provides an immunoassay for measuring the amount of a mammalian glutamylcysteine synthetase in a biological sample comprising steps of: a) contacting the biological sample with at least one antibody, either monoclonal or polyclonal, to form a complex with said antibody and the glutamylcysteine synthetase, and b) measuring the amount of the glutamylcysteine synthetase in said biological sample by measuring the amount of said complex.

BRIEF DESCRIPTION OF FIGURES

FIG. 2 pLAldo-X Plasmid Construction.

FIG. 3 Maphosphamide-resistance of pLAldo-SN transduced K562 cells (Lozzio and Lozzio, 1975). MPA is maphosphamide. The graph represents the mean value of three different is experiments±standard deviations.

FIGS. 4A–4G Nucleotide sequence of the 1842 bp full-length Aldehyde dehydrogenase (Aldh-1) cDNA sequence (SEQ. ID. NO. 1). The translation initiation codon (ATG) is preceded by an in frame translation stop codon, tag (underlined).

FIG. 5A through FIG. 5E Aldehyde dehydrogenase (Aldh-1) amino acid sequence (SEQ. ID. NO. 2).

FIG. 6A through FIG. 6I Nucleotide sequence of the 2904 bp full length glutamylcysteine synthetase (γ-GCS) cDNA sequence (SEQ. ID. NO. 3). The translation initiation codon (ATG) is preceded by an in frame translation stop codon, tga (underlined).

FIGS. 7A–7F Glutamylcysteine synthetase (γ-GCS) amino acid sequence (SEQ. ID. NO. 4).

DETAILED DESCRIPTION OF INVENTION

Figure 1:
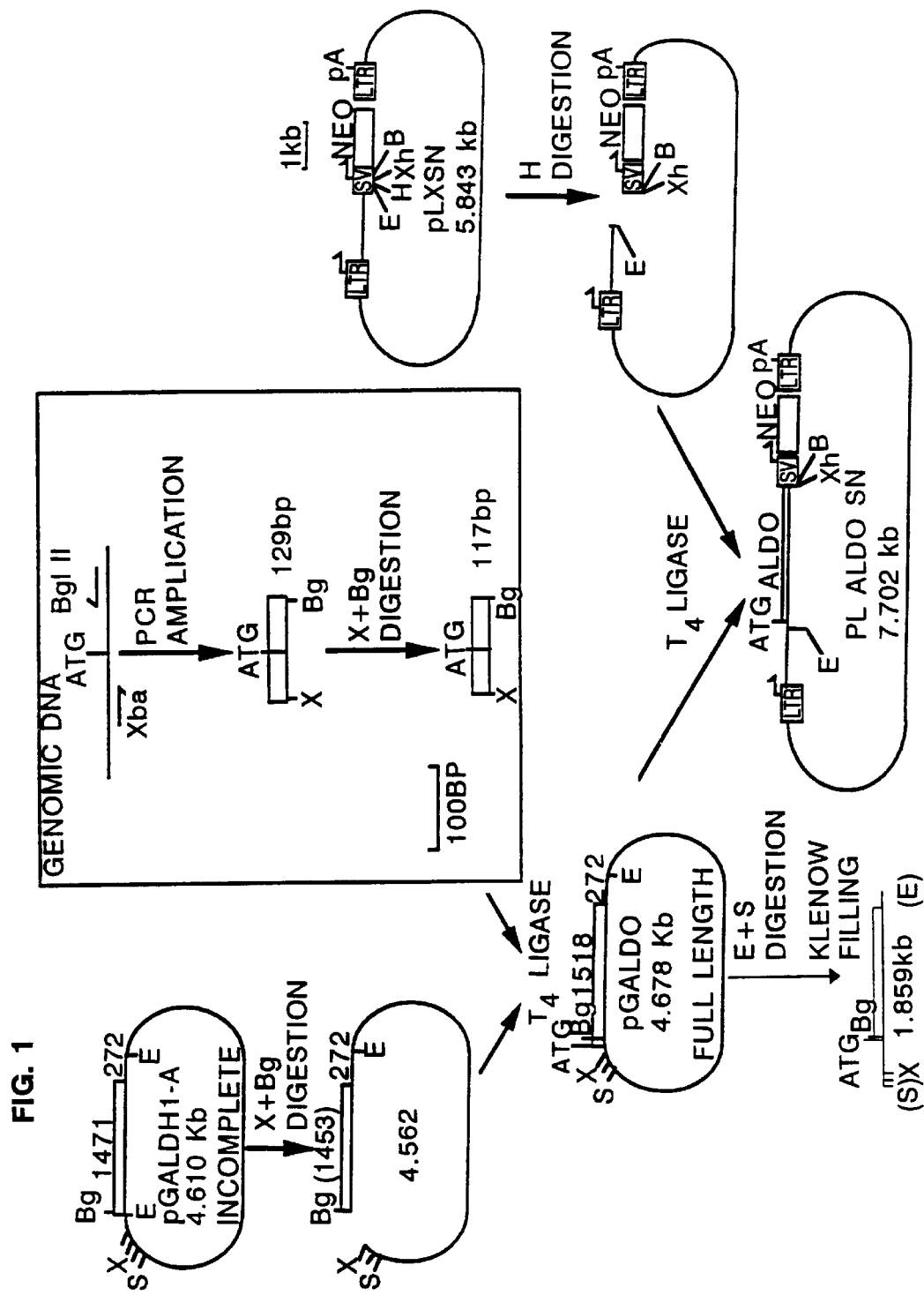
FIG. 1 pLAldo-SN Plasmid Construction, where ALDH1 =Human cytosolic aldehyde dehydrogenase 1, pG=pGEM, B=BamH1, Bg=BglII, S=SalI, E=EcoRI, X=XbaI, Xh=Xhol, H=HpaI.

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |

A "gene" means a nucleic acid molecule, the sequence of which includes all the information required for the normal regulated production of a particular protein, including the structural coding sequence, promoters and enhancers.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention provides a vector which comprises a nucleic acid molecule encoding a human cytosolic aldehyde dehydrogenase inserted into a site within a region of the vector which is not essential for its replication. The vector may be a viral vector. Further, the viral vector may be a double-stranded DNA viral vector.

In one embodiment, the above described nucleic acid molecules are RNA. In another embodiment, the nucleic acid molecules are DNA. In a further embodiment, the DNA molecules are genomic. In a still further embodiment, the DNA molecules are cDNAs. Further, the nucleic acid molecule encoding the cytosolic aldehyde dehydrogenase may be substantially the same sequence shown in FIGS. 4A–4G (SEQ ID NO: 1).

In addition, this invention provides a retroviral vector, which comprises a nucleic acid molecule encoding a human cytosolic aldehyde dehydrogenase inserted into a site within a region of the vector which is not essential for its replication. The vector may be a retroviral vector. Further, the retroviral vector may be a double-stranded DNA retroviral vector.

As used in this invention, human cytosolic aldehyde dehydrogenase is used interchangeably with human aldehyde dehydrogenase 1. In addition, a human cytosolic aldehyde dehydrogenase means a full length human cytosolic aldehyde dehydrogenase.

This invention provides the above described retroviral vector, wherein the vector comprises DNA from a murine virus corresponding to two long terminal repeats, and a packaging signal. In an embodiment, the murine virus is Moloney murine leukemia virus. In another embodiment, the murine virus is Maloney murine sarcoma virus. In a further embodiment, the 3' long terminal repeat corresponds to that present in Maloney murine leukemia virus and the 5' long terminal repeat corresponds to that present in Maloney murine sarcoma virus.

Vectors include but are not limited to: adenovirus, simian virus 40 (SV40), cytomegalovirus (CMV), mouse mammary tumor virus (MMTV), Malony murine leukemia virus, murine sarcoma virus, and Rous sarcoma virus, DNA delivery systems, i.e liposomes, and expression plasmid delivery systems.

It is well known in the art that the packaging signal may contain splice donors and splice acceptors which are important for gene expression.

The retroviral vector may further comprise a DNA sequence corresponding to a second mammalian gene. The second mammalian gene is derived from mammalian cells and encodes a protein normally expressed in mammalian cells. The second mammalian gene may be a cDNA sequence operably linked to a promoter of DNA expression or a genomic DNA sequence. In one embodiment of this invention, the second mammalian gene is a gene encoding a non-selectable phenotype. As used herein, a "non-selectable phenotype" means the expression of a gene which cannot be selected for by any of the conventional means, i.e., with drugs, heat or other conventionally used selection pressures. A non-selectable phenotype means that systems containing a mixture of cells, some of which contain cells positive for the non-selectable phenotype and some of which are negative, cannot be manipulated by conventional means such that only cells positive for the non-selectable phenotype survive the manipulation. Genes encoding a non-selectable phenotype useful in accordance with the practice of this invention include insulin, β-globin and major histocompatibiltiy genes. However, the practice of this invention is not limited to the insertion of only these genes into the retroviral vector. Other mammalian genes suitable for inclusion in a retroviral vector and insertion into a mammalian cell are also encompassed by the practice of this invention.

The second mammalian gene will be packed by the retroviral packaging cell into retroviral particles by virtue of its inclusion in the retroviral vector. Selection of retroviral packaging cells capable of producing a sufficiently high titer of retroviral particles enables the cell to be used in a method of transducing a recipient cell with the gene of interest. (Banket et al. U.S. Pat. No. 5,278,056, issued Jan. 11, 1994.)

In addition, this invention provides a vector which comprises a nucleic acid molecule encoding a human glutamylcysteine synthetase inserted into a site within a region of the vector which is not essential for its replication. The vector may be a viral vector. Further, the viral vector may be a double-stranded DNA viral vector.

In one embodiment, the above described nucleic acid molecules are RNA. In another embodiment, the nucleic acid molecules are DNA. In a further embodiment, the DNA molecules are genomic. In a still further embodiment, the DNA molecules are cDNAs. Further, the nucleic acid molecule encoding the glutamylcysteine synthetase may be substantially the same sequence shown in FIGS. 6A–I (SEQ ID NO: 3).

In addition, this invention provides a retroviral vector, which comprises a nucleic acid molecule is encoding a human glutamylcysteine synthetase inserted into a site within a region of the vector which is not essential for its replication. The vector may be a retroviral vector. Further, the retroviral vector may be a double-stranded DNA retroviral vector.

In one embodiment, this invention provides a plasmid which comprises the double-stranded DNA retroviral vector which comprises cDNA encoding a human cytosolic aldehyde dehydrogenase inserted into a site within a region of the vector which is not essential for its replication.

In addition, this invention provide s a plasmid which comprises the aldehyde dehydrogenase or glutamylcysteine synthetase viral vector or retroviral vector. In an embodiment, the plasmid is designated pLAldo-SN (ATCC Accession No. 69238). The plasmid, pLAldo-SN was introduced into E. coli HB101 and deposited with the American Type Culture Collection (ATCC), 12301 Parktawn Drive, Rockville, Md. 20852, U.S.A. on Feb. 10, 1993 under the provisions of the Budapest Treaty for the International Recognition of the Deposit of Microorganism for the Purposes of Patent Procedure. The E. coli HB101 containing pLAldo-SN was accorded with ATCC Accession number 69238. In another embodiment, the plasmid is designated pLAldoX.

In addition, this invention provides, a plasmid designated pLGCS-X (ATCC Accession No. 69596). The plasmid, pLGCS-X was introduced into E. coli DH5α and deposited with the American Type Culture Collection (ATCC), 12301 Parklawn Drive, Rockville, Md. 20852, U.S.A. on Mar. 24, 1994 under the provisions of the Budapest Treaty for the International Recognition of the Deposit of Microorganism for the Purposes of Patent Procedure.

This invention also provides a mammalian retroviral producer cell which comprises the double-stranded DNA retroviral vector having cDNA encoding a human cytosolic aldehyde dehydrogenase inserted into a site within a region of the vector which is not essential for its replication, the plasmid, pLAldo-SN or the plasmid, pLAldoX.

In one embodiment, pALAldo-SN is introduced into the PA317 cell and the producer cell formed is designated, pLAldo-SN PA317cl.6. This cell line, pLAldo-SN PA317cl.6, was deposited with the American Type Culture Collection (ATCC), 12301 Parklawn Drive, Rockville, Md. 20852, U.S.A. on Feb. 10, 1993 under the provisions of the Budapest Treaty for the International Recognition of the Deposit of Microorganism for the Purposes of Patent Procedure. The PA317 cell containing pLAldo-SN was accorded with ATCC Accession number CRL 11265.

This invention also provides a human cell which comprises the double-stranded DNA retroviral vector which comprises CDNA encoding a human cytosolic aldehyde dehydrogenase inserted into a site within a region of the vector which is not essential for its replication, the plasmid, pLAldoX or the plasmid, pLAldo. In one embodiment, the human cell is a human hematopoietic cell. In another embodiment, the human cell is a bone marrow cell.

In addition, this invention provides a host vector system for the production of a polypeptide having the biological activity of a cytosolic aldehyde dehydrogenase which comprises a plasmid and a suitable host. The host vector system may be a bacterial cell, insect cell, viral cell or mammalian cell. The plasmid may be a pLALdo-SN or pLAldoX as hereinabove discussed.

The nucleic acid molecule may be a DNA, RNA, cDNA. Further, the nucleic acid molecule encoding the human cytosolic aldehyde dehydrogenase may have substantially the same sequence shown in FIGS. 4A–4G (SEQ ID NO: 1).

Further, this invention provides a host vector system for the production of a polypeptide having the biological activity of an glutamylcysteine synthetase which comprises a plasmid and a suitable host.

In addition, this invention provides a method for introducing a selectable marker into a mammalian cell which comprises transfecting the cell with a nucleic acid molecule encoding human glutamylcysteine synthetase. The nucleic acid molecule may be a DNA, RNA or cDNA molecule.

The nucleic acid molecule may be a DNA, RNA, or cDNA. Further, the nucleic acid molecule encoding the human glutamylcysteine synthetase may have substantially the same sequence shown in FIGS. 6A–I (SEQ ID NO: 3).

This invention provides a method for reducing the toxic effects of a cyclophosphamide in a subject which comprises replacing the subject's hematopoietic cells with hematopoietic cells which carries the cytosolic aldehyde dehydrogenase gene so as to reduce the toxic effects of the cyclophosphamide in the subject.

As used herein, a cyclophosphamide is cyclophosphamide or a derivative or homolog thereof which is effective as a cancer chemotherapeutic agent through the same mechanism or mode of action as cyclophosphamide. One example of such derivative is maphosphamide.

One method to produce hematopoietic cells which carry the cytosolic aldehyde dehydrogenase (Aldh1) is to introduce the double-stranded DNA retroviral vector which comprises cDNA encoding a human cytosolic aldehyde dehydrogenase inserted into a site within a region of the vector which is not essential for its replication into hematopoietic cells. The retroviral vector carrying the Aldh1 gene may be introduced to a packaging cell to generate a virus producing cell line. The viruses generated may then be used to infect hematopoietic cells. Other ways for introducing the ALDH1 gene well known to a person of ordinary skill in the art are included by this invention. One such method is electroporation and others including but are not limited to calcium phosphate precipitation technology, other viral vector systems such as adeno-associated virus system, lipofection and microinjection may be used in accordance with this invention.

This invention further provides a method for introducing a selectable marker into a mammalian cell which comprises transfecting the cell with DNA encoding human cytosolic aldehyde dehydrogenase.

In addition, this invention provides a method for selecting mammalian cells expressing a protein of interest which comprises a) introducing into the cells a DNA molecule comprising DNA encoding the protein of interest and DNA encoding human cytosolic aldehyde dehydrogenase; b) culturing the resulting transfected cells; and c) selecting cells which express human cytosolic aldehyde dehydrogenase, so as to obtain cells which express the protein of interest. In an embodiment, the DNA molecule of step (a) of the above described method is part of a retroviral vector.

In addition, this invention provides a method for selecting mammalian cells expressing a protein of interest which comprises: a) introducing into the cells a nucleic acid molecule comprising a nucleic acid molecule encoding the protein of interest and the nucleic acid molecule encoding human glutamylcysteine synthetase; b) culturing the resulting transfected cells; and c) selecting cells which express human glutamylcysteine synthetase, so as to obtain cells which express the protein of interest. The nucleic acid molecule may be a DNA, RNA or cDNA molecule.

The nucleic acid molecule may be a DNA, RNA, or cDNA. Further, the nucleic acid molecule encoding the human glutamylcysteine synthetase may have substantially the same sequence shown in FIGS. 6A–I (SEQ ID NO: 3).

In addition, this invention provides an isolated mammalian nucleic acid molecule encoding a cytosolic aldehyde dehydrogenase. The isolated mammalian nucleic acid molecule may have substantially the same sequence shown in FIGS. 4A–4G (SEQ ID NO: 1). The isolated nucleic acid molecule may be a DNA, RNA, or CDNA. Further, the isolated nucleic acid molecule may be derived from a human.

In addition, this invention provides an isolated mammalian nucleic acid molecule encoding a glutamylcysteine synthetase. The isolated mammalian nucleic acid molecule may have substantially the same sequence shown in FIGS. 4A–G (SEQ ID NO: 1). The isolated nucleic acid molecule may be a DNA, RNA, or CDNA. Further, the isolated nucleic acid molecule may be derived from a human.

In addition, this invention provides a nucleic acid molecule of at least 15 nucleotides capable of specifically hybridizing with a sequence of the nucleic acid molecule of the isolated mammalian nucleic acid molecule encoding a cytosolic aldehyde dehydrogenase or a glutamylcysteine synthetase. The nucleic acid molecule may be a DNA, RNA, or cDNA.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encode aldehyde dehydrogenase into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

In addition, this invention provides a method of detecting expression of an aldehyde dehydrogenase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian cytosolic aldehyde dehydrogenase which comprises growing the host cells of the host vector system under suitable conditions permitting production of the polypeptide and recovering the polypeptide so produced.

In addition, this invention provides a method of detecting expression of a glutamylcysteine synthetase in a cell which comprises obtaining total mRNA from the cell, contacting the mRNA so obtained with a labelled nucleic acid molecule of the isolated mammalian nucleic acid molecule encoding an glutamylcysteine synthetase under hybridizing conditions, determining the presence of mRNA hybridized to the molecule, and thereby detecting the expression of the glutamylcysteine synthetase in the cell.

In addition, this invention provides a method of producing a polypeptide having the biological activity of a mammalian glutamylcysteine synthetase which comprises growing the host cells of the host vector system under suitable conditions permitting production of the polypeptide and recovering the polypeptide so produced.

Numerous mammalian cells may be used as hosts, including, but not limited to, the mouse fibroblast cell NIH 3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the mammalian aldehyde dehydrogenase may be otherwise introduced into mammalian cells, e.g., by microinjection, to obtain mammalian cells which comprise DNA, e.g., cDNA or a plasmid, encoding a mammalian aldehyde dehydrogenase.

In addition, this invention provides an antibody directed against the amino acid molecule of a cytosolic aldehyde dehydrogenase. The amino acid sequence may be substantially the same as shown in FIGS. 5A–E (SEQ ID NO: 2). The antibody may be a monoclonal or a polyclonal antibody.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian aldehyde dyhydrogenase in living animals, in humans, or in biological tissues or fluids isolated from animals or humans.

In addition, this invention provides an antibody directed against the amino acid molecule an glutamylcysteine synthetase. The amino acid sequence may be substantially the same as shown in FIGS. 7A–7F (SEQ ID NO: 4). The antibody may be a monoclonal or a polyclonal antibody.

In addition, this invention provides an immunoassay for measuring the amount of a mammalian cytosolic aldehyde dehydrogenase in a biological sample comprising steps of: a) contacting the biological sample with at least one antibody, either monoclonal or ployclonal, to form a complex with said antibody and the cytosolic aldehyde dehydrogenase, and b) measuring the amount of the cytosolic aldehyde dehydrogenase in said biological sample by measuring the amount of said complex.

In addition, this invention provides a transgenic nonhuman mammal which comprises the isolated mammalian nucleic acid molecule encoding an cytosolic aldehyde dehydrogenase.

In addition, this invention provides a transgenic nonhuman mammal whose genome comprises antisense DNA complementary to DNA encoding a cytosolic aldehyde dehydrogenase so placed as to be transcribed into antisense mRNA complementary to mRNA encoding the cytosolic aldehyde dehydrogenase and which hybridizes to mRNA encoding the mammalian cytosolic aldehyde dehydrogenase thereby reducing its translation. Further, the isolated nucleic acid molecule encoding the human cytosolic aldehyde dehydrogenase may have substantially the same sequence shown in FIG. 4 (SEQ ID NO: 1).

In addition, this invention provides an immunoassay for measuring the amount of a mammalian glutamylcysteine synthetase in a biological sample comprising steps of: a) contacting the biological sample with at least one antibody, either monoclonal or ployclonal, to form a complex with said antibody and the glutamylcysteine synthetase, and b) measuring the amount of the glutamylcysteine synthetase in said biological sample by measuring the amount of said complex.

In addition, this invention provides a transgenic nonhuman mammal which comprises the isolated mammalian nucleic acid molecule encoding a glutamylcysteine synthetase.

In addition, this invention provides a transgenic nonhuman mammal whose genome comprises antisense DNA complementary to DNA encoding a glutamylcysteine synthetase so placed as to be transcribed into antisense mRNA complementary to mRNA encoding the glutamylcysteine synthetase and which hybridizes to mRNA encoding the mammalian glutamylcysteine synthetase thereby reducing its translation. Further, the isolated nucleic acid molecule encoding the human cytosolic aldehyde dehydrogenase may have substantially the same sequence shown in FIGS. 4A–4G (SEQ ID NO: 3).

One aim of this invention is as follows: Chemotherapy with specific anticancer drugs represents a broadly used and very effective treatment modality for a variety of human cancers. However, most chemotherapeutic treatments have side-effects that severely limit their efficacy and cause risks in their usage. In particular, chemotherapy-induced cytopenia, i.e. the suppression of normal hematopoiesis (myelosuppression) leading to decreased production of leukocytes and platelets, represents a major factor of morbidity, mortality and underdosing in cancer treatment. It is conceivable that the ability to eliminate chemotherapy-induced cytopenia will lead both to decreased risk in cancer chemotherapy and, most notably, to the possibility of higher-dose treatment leading to higher cure rates.

This invention aims at solving the problem of cytopenia induced by the widely used chemotherapeutic drug cyclophosphamide (CP) and its analogs. CP is an anticancer drug with marked activity on a wide range of human tumors. Its activity is dose-dependent with a steep dose-response relationship and its dose-limiting toxicity is myelosuppression. Currently available strategies for treating CP-induced cytopenia are indirect and mainly based on accelerating the recovery of depressed hematopoiesis by using specific growth factors capable of stimulating bone marrow regeneration. The proposed invention is aimed at directly overcoming cyclophosphamide-induced cytopenia by rendering the hematopoietic cells resistant to the toxic effects of the drug.

One strategy of this invention is to make hematopoietic cells resistant to cyclophosphamide (CP) and its analogs by the introduction and expression of a gene whose protein product can metabolize CP into non-toxic and inactive compounds. Several lines of investigations have suggested that aldehyde dehydrogenase (Aldh) is involved in CP metabolism and resistance: i) cytotoxic metabolites of CP are generated via an aldehyde-containing intermediate that can be inactivated by Aldh (Struck et al., 1975; Colvin et al., 1976; Cox et al., 1975; Hill et al., 1972); ii) a correlation has been repeatedly observed between the levels of Aldh activity and the ability of various cell lines to resist to the CP toxicity (Cox et al., 1975; Hilton, 1984; Lin et al., 1988; iii) inhibitors of Aldh activity increase the sensitivity to CP toxicity (Sladek and Landkamer, 1985; Kohn and Sladek, 1987; Sahovic et al., 1988). In addition, it has been demonstrated that while the most immature hematopoietic cells express Aldh1, this activity is progressively downregulated in their functionally mature progeny including leukocytes, platelets and erythrocytes (Kastan et al., 1990), correlating with their sensitivity to CP. Thus, the stable expression of Aldh1 in hematopoietic precursors should make them and their progeny resistant to CP.

Based on these observations, a retroviral vector has been designed which carries and can express the human Aldh-1 gene. Retroviral vectors can transduce genes into human hematopoietic precursors (Bregni et al., 1992) which are used for bone marrow repopulation by autologous bone transplantation after chemotherapeutic treatment (Gianni et al., 1989).

One objective of this invention is to construct a retroviral vector capable of conferring resistance to the anti-cancer drug cyclophosphamide. This will be done by using the human aldehyde dehydrogenase gene which has been shown to confer resistance to cyclophosphamide and its anti-cancer analogs. A full-length cDNA for human Aldh1 is now isolated and used to construct a first vector which is shown to be capable of transducing the specific drug resistance phenotype to a variety of target cells including human CD34+ cells in vitro (FIGS. 4A–G SEQ ID NO:1) (See Experimental Details I).

Chemotherapeutic Agents, include but are not limited to: Alkylating Agents, i.e. Nitrogen Mustards, Ethylenimines and Methylemelamines, Alkyl Sulfonates, Nitrosoureas, and Triazenes. Further chemotherapeutic agents include antimetabolites, i.e. Folic Acid Analogs, Pyrimidine Analogs, Purine Analogs and Related Inhibitors.

Further chemotherapeutic agents include natural products, i.e. Vinca Alkaloids, Epipodophyllotoxins, Antibiotics, Enzymes, Biological Response Modifiers. Further, chemotherapeutic agents include miscellaneous Agents, i.e. Plantinum Coordination Complexes, Anthracenedione, Substituted Urea, Methyl Hydrazine Derivative, and Adrenocortical Suppressant. Lastly, chemotherapeutic agents include hormones and antagonists, i.e. Adrenocorticosteroids, Progestins, Estrogens, Antiestrogen, Androgens, Antiandrogen, and Gonadotropin-releasing hormone analog.

In addition to its use in anti-cancer therapeutic protocols, a number of observations suggest that the ALDH gene can be used as a general selectable marker to select transduced cells both in vivo and in vitro using CP as a selection agent: i) CP exhibits marked cytotoxic activity on a wide range of eukaryotic cells in vitro; ii) the emergence of drug resistance to alkylating agents is a relatively rare and late event particularly in vitro; iii) CP kills sensitive cells after short exposure and the effect becomes evident within a very short time. Therefore, retroviral vectors carrying the Aldh gene and a second relevant gene to be expressed can be used for the selection of transduced cells in vitro as well as for the selection of transduced cells from a variety of tissue targets in vivo. This latter application is likely to be useful in the context of a variety of gene therapy protocols whenever a strong and continued selection of the transduced cells is necessary. The fact the CP is an already approved drug in humans represents an additional advantage of this strategy.

The Aldh1 gene can serve as a dominant selectable marker to permit both the in vitro and in vivo selection of cells transformed with a second gene of interest. The need for a selectable marker gene in gene transfer experiments stems from the usually low transfer efficiency and the high frequency of mutations and rearrangements leading to rapid functional inactivation of transduced gene. A selectable marker gene thus provides the means for expanding the usually small proportion of cells that have incorporated the gene of interest and are capable of expressing it in a functional form over time. The development of a selection system applicable to as wide a range of target cells as possible has become a central goal of gene transfer research, as clearly indicated by the substantial and growing number of different proposals.

The Aldh1 gene promises to represent an invaluable dominant selectable marker after co-transduction with an unrelated, unselectable gene of interest into cyclophosphamide-sensitive cells. To correct a genetic disease like ADA deficiency or β-thalassemia, it is essential to develop a strategy for the preferential in vivo expansion of the small number of hematopoietic stem cells that can be transduced with the relevant defective gene (i.e., the ADA or β-globin genes, with or without regulatory sequences). In fact, even an hypothetical 100% transduction efficiency of the small number of harvested stem cells used for in vitro manipulation experiments would represent a minor fraction of the overall pool of resident stem cells, left unchanged in the host bone marrow. To favor the engraftment of transduced cells by destroying the recipient bone marrow with ionizing radiations and/or myeloablative drugs is least acceptable in non-neoplastic diseases like ADA deficiency and β-thalassemia. Cyclophosphamide is an alkylating agent widely employed also in non-neoplastic diseases (i.e. autoimmune diseases) and its use according to standard doses and schedules is safe and devoid of major acute and chronic toxicities. Its short term administration over a number of courses to patients autografted with bone marrow cells transduced with a vector containing both ADA and ALDH genes is thus expected to confer a selective advantage to the infected cells, allowing their preferential in vivo expansion. The same principle applies to different models of gene therapy in which the target cell is cyclophosphamide-sensitive (i.e. T-lymphocytes, tumor cells, etc.) (for a review, see W. F. Anderson, 1992).

The Aldh1 gene may be used as a selectable marker to introduce the human glutamylcysteine synthetase gene to generate cells capable of conferring resistance to anti-cancer alkylating agent such as cis-platinum, melphalan, ionizing radiations. The expression of human gamma-glutamylcysteine synthetase gene (γ-GCS) has been shown to correlate with the acquisition of resistance to alkylating agents in a variety of tumor cell lines in vitro. The Aldh gene may be used as a selectable marker to facilitate the introduction of the γ-GCS genes into cells.

Another example is to generate cells which are capable of conferring resistance to human immunodeficiency virus (HIV) infection. DNA sequences coding dominant negative products or anti-sense RNAs capable of interfering at various levels with HIV infection may be introduced into CD34+ cells using Aldh1 gene as a selectable marker. The introduction of these DNA sequences should constitute an HIV-resistant T cell compartment in vivo.

One method to use the Aldh1 gene as selectable marker includes inserting the Aldh1 gene and at least one gene of interest into a retroviral vector. The retroviral vector carrying the Aldh gene and the gene of interest may be introduced to a packaging cell to generate a virus producing cell line. The viruses generated may then be used to infect cells. Other ways of introducing a selectable marker into cells known in the art are included by this invention. One such method is electroporation and others including but are not limited to calcium phosphate precipitation technology, other viral vector systems such as adeno-associated virus system, lipofection and microinjection may be used in accordance with this invention.

To summarize, a retroviral vector carrying the Aldh1 gene can be used: i) to confer CP resistance to hematopoietic cells and their progeny allowing for treatment with high-dose CP in anti-cancer therapeutic regimens; ii) to use CP-resistance as a general marker for the selection of retrovirally transduced cells in vitro or in vivo.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Construction of retroviral vector which carries the aldehyde dehydrogenase gene A. pLAldo-SN Plasmid Construction (FIG. 1)

1) Cloning of human cytosolic aldehyde dehydrogenase (Aldh1) full length cDNA

A human liver cDNA library from Clonentech (HL1115A) was screened with a partial cDNA probe, kindly donated by L. C. Hsu (Hsu, L., et al., 1985). The probe, named Aldh1, corresponds to 1020 bp coding and 540 bp 3' flanking sequences.

A partial CDNA clone, pGA1dh1-A, was isolated with 1471 bp of coding sequences and 272 bp 3' flanking which lack 46 bp to the ATG.

In order to obtain the remaining 5' sequences, a PCR amplification on genomic DNA was achieved using a 5' end primer designed on the genomic sequence (Hsu, et al., 1989) and a 3' end primer based on the available sequence. The primers contain Xba I and Bgl II sites for cloning purposes. The PCR product, after Xba I and Bgl II digestion, was subcloned into pGA1dh1-A leading to plasmid containing the full length cDNA, pGA1do, of 1518 bp coding sequences, in which the natural Bgl II site 5' to PGA1DH1-A and 3' to the genomic PCR product are used to conserve the reading frame.

2) Construction of a retroviral vector plasmid carrying the human cytosolic aldehyde dehydrogenase gene.

The human cytosolic aldehyde dehydrogenase full length cDNA Aldo, (FIGS. 4A–4G, SEQ ID NO: 1), derived from Eco RI and Sal I digestion of pGA1do and filling of the 3' recessive ends was subcloned into Hpa I of pLXSN, an amphotropic retroviral vector kindly donated by D. Miller (Miller, D., and Rosman, G., 1989) to generate pLAldo-SN.

E. pLAldoX Plasmid Construction (FIG. 2)

The human cytosolic aldehyde dehydrogenase full length cDNA, Aldo, derived from Eco RI and Sal I digestion of pGA1do and filling of the 3' recessive ends were subcloned into the pLNSX vector containing a neomycin gene, obtained from Dr. Miller (Miller, D., and Rosman, G., 1989). The derived plasmid contains 6,137 base pairs. The neomycin gene was cut out by BclI digestion. The digested vector was then filled-in, further digested with StuI, treated with calf-intestinal phosphatase (CIP) and LMP-purified. This digested vector was then ligated with the previously purified pAldo fragment containing the Aldehyde Dehydrogenase-1 Gene. The Aldehyde Dehydrogenase-1 gene was placed downstream of the vector's 5' LTR and the plasmid so formed is called pLAldoX which is 6,495 basepair long.

C. Generation of the retrovirus

In order to generate amphotropic retroviral vector carrying Aldo, the plasmid pLAldo-SN was transfected into the ψ2 ecotropic packaging cell line (obtained from Mulligan, R. (Mann, et al., (1983) Cell 33:153–159) by the CaPO4 precipitation procedure. After 48 hours the supernatant of the transfected cell line which contained the ecotropic Aldo-SN virus was used to infect the amphotropic packaging cell line PA317 (obtained from ATCC CRL 9078) (Miller, D., and Buttimore, C., (1986) Mol. Cell. Biol. 6:2895). The infected cells were selected in neomycin containing medium and 30 clones were isolated for further characterization for virus titer and Aldh1 RNA expression. pLAldo-SN PA317 cl.6, 22 and 3 were shown to have the highest titer and Aldh1 RNA expression.

The above experiment was done using the plasmid, pLAldo-SN. Retroviruses may also be generated similarly using the plasmid pLAldoX.

II. Demonstration of Maphosphamide-resistance in pLAldo-SN transduced cells.

1) Infection of K562 cells.

Virus-containing supernatant from pLAldo-SN PA317 cl.6 cells was used to infect K562 cell, a human pluripotent leukemic cell line. Wild type (ctr) and pLAldo-SN infected K562 cells were exposed to different concentrations of maphosphamide (MPA) for 30 minutes at 37° C. at $1 \times 10^6$ cells/ml and then plated at $3–5 \times 10^3$ cells/plate in 0.3% agar in 35 mm plates. MPA-resistance was scored as % of the colonies growing from MPA-selected vs unselected cells after 12 days of incubation at 37° C. and 5% $CO_2$. The graph in FIG. 3 represents the mean value of three different experiments±standard deviations. The results indicate that pLAldo-SN transduced K562 cells display increased resistance to MPA at concentrations ranging from 20 to 80 $\mu$M.

2) Infection of normal human hematopoietic progenitor cells.

Human hematopoietic progenitor cells, obtained by leukapheresis followed by ficoll-hypaque centrifugation, were preincubated for two days in Iscove Modified Dulbecco Medium (IMDM)+20% FCS+IL3+IL6 and then infected with different supernatants from PA317-pLAldo-SN clones. Cells were then exposed for 30 minutes at 37° C. to 5 $\mu$M of maphosphamide (MPA) at $1 \times 10^6$ cells/ml and plated in 60 wells of a 96 multiwell plates at 100 cells/well in IMDM+ 20% FCS+5637 CM 10% (bladder carcinoma conditioned media)+IL3+IL6+GM–CSF+idrocortisone $10^{-6}$M. MPA-resistance was scored as number of positive wells growing after 12 days of incubation at 37° C. and 5% CO2.

The results, showed in the following Table 1 indicate that three different LAldo-SN viral clones (originated from the corresponding PA317-pLAldo-SN cell clones) were able to confer MPA-resistance scored as the number of cells capable of growing after MPA treatment.

TABLE 1

Maphosphamide-resistance of pLAldo-SN-transduced human hematopoietic progenitor cells

| Samples | Number of positive wells −MPA | +MPA | MPA resistance % wells |
|---|---|---|---|
| Control | 58 | 5 | 8.6 |
| cl.22-infected | 60 | 15 | 25 |
| cl.6-infected | 60 | 20 | 33 |
| cl.3-infected | 60 | 41 | 68 |

III. Uses of the human cytosolic aldehyde dehydrogenase gene as selectable marker in vivo.

Construction of a retroviral vector carrying the human cytosolic aldehyde dehydrogenase gene and the human glucocerebrosidase (GCase) gene. Aldo-GCase retroviral vector can be generated from the NTG plasmid (Correll, 1989) by removing the neo selectable marker and by inserting the coding sequence for the human cytosolic aldehyde dehydrogenase gene.

Human hematopoietic progenitor cells can be obtained by leukapheresis from a Gaucher disease patient treated with r-hu-IL3 (7 days at 5 g/kg/day continuous iv induction) following by either rhGM-CSF or rhG-CSF for 3–5 additional days (both at 5 g/kg/day). Daily leukaphereses can be repeated until $3 \times 10^9$ CD34+ cells (Siena et al., 1991) are harvested.

Light-density cells from each leukapheresis are obtained by Ficol-Hypaque centrifugation and infected with clinical-grade supernatant from PA317 clones producing high-titer Aldo-GCase vector free of helper virus.

Following infection, aliquots from each leukapheresis can be exposed for 30 minutes at 37° C. to 5 $\mu$M MPA and plated as described above. Twelve days later, MPA resistance are scored to assess the efficiency of transduction.

The bulk of infected cells can be washed by centrifugation and immediately reinfused without freezing. In vivo treatment with cyclophosphamide starts only 12 days later, following assessment of the proportion of MPA-resistant clones. Only in case of infection efficiency 30% (Bregni, et al., 1992) the patient can be treated with cyclophosphamide.

Two different selection protocols are sequentially tested. According to the first protocol, cyclophosphamide can be given at 100 mg/m2 per day for 14 consecutive days, as per standard schedules adopted in combination chemotherapy (Canellos et al., 1976). Before treatment, a bone marrow aspirate can be obtained to determine baseline frequency of Aldo-GCase infected and MPA-resistant clones. Bone marrow aspirate is repeated at the end of treatment and results compared with baseline data. If no or minor changes in the proportion of transfected cells are observed, and cells carrying the Aldo-GCase gene are identified, a different protocol using high-dose cyclophosphamide can be tested. Five to seven g/m2 cyclophosphamide are infused following by reGM-CSF or rhG-CSF administration (Gianni et al., 1990). The infusions can last longer than described (24 instead of 12 hours) to prevent cyclophosphamide concentration from rising about 5 $\mu$M. The expansion of MPA-positive bone marrow colonies are assessed before and after cyclophosphamide treatment by both PCR and MPA-resistance.

Figure 8:
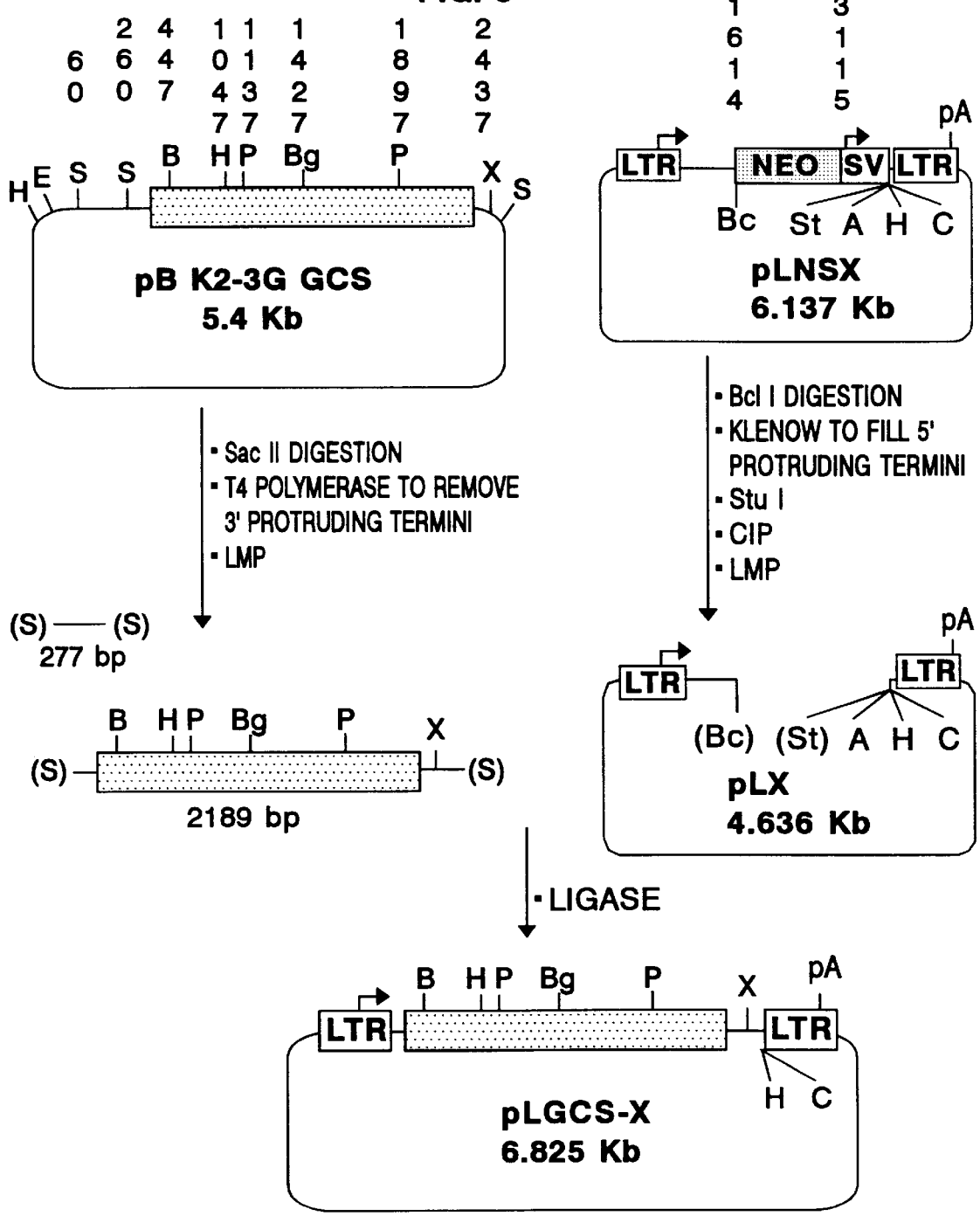
FIG. 8 pLGCS-X Plasmid Construction.

IV. Construction of retroviral vector which carries the glutamylcysteine synthetase gene A. pLGCS-X Plasmid Construction (FIG. 8)

In order to obtain a full-length γ-GCS CDNA, a human kidney cDNA library (Clonentech, HL 1123) was screened with a partial γ-GCS cDNA probe (Pst I fragment, nucleotides 1 137–1897 in the sequence shown in FIG. 2) obtained from R. T. Mulcahy. The inserts of two overlapping cDNA clones together spanning 2904 bp. of cDNA sequence were ligated using an internal Hind III site (position 1047) to generate the plasmid pB K2–3G GCS (FIG. 8). This plasmid was then digested with Sac I, the 3' protruding ends were filled using T4 polymerase and the insert was isolated by preparative electrophoresis in low melting point (LMP in Gig. 3) agarose. The fragment was then ligated using T4 ligase to the blunt ends of the pLX vector obtained by BclI digestion, 5' protruding fill-in by Klenow fragment polymerase, StuI digestion, and dephosphorylation by calf intestine phosphatase) to generate the pLGCS-X vector.

REFERENCES

Anderson, W. F., (1992) 256:808.
Bregni, M, Magni, M., Siena, S., Di Nicola, M., Bonadonna, G., Gianni, A. M., (1992) Blood, 80:1418.
Canellos, et al (1976) Cancer 38:1882.
Colvin, M., Brundrett, R. B., Kan, M-N. N., Jardine, I., and Fenselau, C., (1976) Cancer Res., 36:1121.
Correll, (1989) PNAS, 86:8912.
Cox, P. J., Phillips, B. J., and Thomas, P., (1975) Cancer Res., 35:3755.
Eglitis (1991) Human Gene Ther. 2:195.
Gianni, A. M., Siena, S., Bregni, M., Tarella, C., Stern, A. C., Pileri, A., and Bonadonna, G., (1989) Lancet, 2:580.
Gianni, et al., (1990) J. Clin. Oncol. 8:768.
Hill, D. L., Laster, W. R., Jr., and Stuck, R. F., (1972) Cancer Res., 32:658.
Hilton, J., (1984) Cancer Res., 44:5156.
Hsu, L. D., et al., (1985) Proc. Natl. Acad. Sci., 82:3771–3775.
Hsu, L. C., et al., (1989) Genomics, 5:857–865.
Kastan, M. B., Schlaffer, E., Russo, J. M., Colvin, O. M., Civin, C. I., and Hilton, J., (1990) Blood, 75:1947.
Khon, et al., (1987) Biochem. Pharmacol., 36:2805.
Lin, K-h, Brennam, M. D., and Lindahl, R., (1988) Cancer Res., 48:7009.
Mann, R. et al., (1983) Cell 33:153.
Miller, D. and Rosman, G., (1989) Biotechniques 7:980–990.2.
Miller, D. and Buttimore, C. (1986) Mol. Cell. Biol. 6: 2895.
Lozzio and Lozzio, (1975) Blood 45:321.
Sahovic, E. A., Colvin, M., Hilton, J., and Ogawa, M., (1988) Cancer Res., 48:1223.
Sladek, N. E., and Landhamer, G. J., (1985) Cancer Res., 45:1549.
Struck, R. P., Kirk, M. C., Wiu, M. H., and Laster, W. H., Jr., (1975) Biomed. Mass Spestrom., 2:46.

What is claimed is:

1. A method for introducing a selectable marker into a mammalian cell which comprises transfecting the cell with an isolated nucleic acid that encodes a human cytosolic aldehyde dehydrogenase which comprises the amino acid sequence set forth in SEQ ID No: 2.

2. The method of claim 1, wherein the isolated nucleic acid is a DNA, RNA or cDNA.

3. The method of claim 2, wherein the isolated nucleic acid has the sequence shown in FIG. 4 (SEQ ID NO: 1).

4. A method for obtaining mammalian cells expressing a protein of interest, the method comprising:
   a. introducing into the mammalian cells a nucleic acid comprising a nucleic acid encoding the protein of interest, and the nucleic acid encoding human cytosolic aldehyde dehydrogenase which comprises the amino acid sequence set forth in SEQ. ID No: 2;
   b. culturing the resulting transfected cells; and
   c. selecting cells which express human cytosolic aldehyde dehydrogenase, so as to thereby obtain cells which express the protein of interest.

5. The method of claim 4, wherein the nucleic acid is DNA, RNA or cDNA.

6. The method of claim 4, wherein the nucleic acid encoding human cytosolic aldehyde dehydrogenase has the sequence shown in FIG. 4 (SEQ ID NO: 1).

7. The method of claim 4, wherein the nucleic acid of step (a) is part of a retroviral vector.

8. The method of claim 1, wherein the nucleic acid encoding human cytosolic aldehyde dehydrogenase is a vector.

9. The method of claim 8, wherein the vector is a retroviral vector.

10. The method of claim 9, wherein the retroviral vector comprises a 3' long terminal repeat which corresponds to the 3' long terminal repeat present in Moloney murine leukemia virus and a 5' long terminal repeat which corresponds to the 5' long terminal repeat present in the Moloney murine sarcoma virus.

11. The method of claim 8, wherein the vector is a plasmid.

12. The method of claim 11, wherein the plasmid is designated pLAldo-SN (ATCC Accession No. 69238).

13. The method of claim 4, wherein the nucleic acid encoding human cytosolic aldehyde dehydrogenase is a vector.

14. The method of claim 13, wherein the vector is a retroviral vector.

15. The method of claim 14, wherein the retroviral vector comprises a 3' long terminal repeat which corresponds to the 3' long terminal repeat present in Moloney murine leukemia virus and a 5' long terminal repeat which corresponds to the 5' long terminal repeat present in the Moloney murine sarcoma virus.

16. The method of claim 13, wherein the vector is a plasmid.

17. The method of claim 16, wherein the plasmid is designated pLAldo-SN (ATCC Accession No. 69238).

* * * * *